United States Patent
Fletcher et al.

(10) Patent No.: US 9,569,846 B2
(45) Date of Patent: Feb. 14, 2017

(54) OPHTHALMIC REFERENCE IMAGE SELECTION

(71) Applicant: CANON KABUSHIKI KAISHA, Tokyo (JP)

(72) Inventors: Peter Alleine Fletcher, Rozelle (AU); Allen Peter Courtney, Mooney Mooney (AU); Dmitri Katchalov, Neutral Bay (AU)

(73) Assignee: CANON KABUSHIKI KAISHA, Tokyo (JP)

( * ) Notice: Subject to any disclaimer, the term of this patent is extended or adjusted under 35 U.S.C. 154(b) by 10 days.

(21) Appl. No.: 14/569,469

(22) Filed: Dec. 12, 2014

(65) Prior Publication Data
US 2015/0170360 A1 Jun. 18, 2015

(30) Foreign Application Priority Data
Dec. 18, 2013 (AU) .................. 2013273657

(51) Int. Cl.
G06K 9/00 (2006.01)
G06T 7/00 (2006.01)
A61B 3/12 (2006.01)

(52) U.S. Cl.
CPC .......... G06T 7/0026 (2013.01); A61B 3/1225 (2013.01); G06T 2207/10016 (2013.01); G06T 2207/30041 (2013.01)

(58) Field of Classification Search
CPC .......... G06T 2207/30041; G06T 2207/10016; G06T 2210/41; G06T 7/0012; G06T 7/0026; A61B 3/00
See application file for complete search history.

(56) References Cited

U.S. PATENT DOCUMENTS 5,680,150 A * 10/1997 Shimizu ............. G06T 3/0081
  345/634
6,830,336 B2 * 12/2004 Fransen ................. A61B 3/14
  351/206

(Continued)

FOREIGN PATENT DOCUMENTS

EP 2114079 A1 11/2009
EP 2005387 B1 12/2012

OTHER PUBLICATIONS

Kubecka, L. et al.; 'Registration of Bimodal Retinal Images—improving modifications'; Department of Biomedical Engineering, Brno University of Technology, Czech Republic; San Francisco, CA, USA • Sep. 1-5, 2004; pp. 1695-1698.

*Primary Examiner* — Tom Y Lu
(74) *Attorney, Agent, or Firm* — Canon USA Inc. IP Division

(57) ABSTRACT

A method for selecting a representative image of an eye from a plurality of captured images, comprises associating neighboring images from the plurality of images with each other to determine a spatial relationship (shift) of the images and an initial quality value for each image. The method determines an accumulated quality value for at least one portion of each image using the initial quality values corresponding to those other images of the plurality of images that are spatially related with the portion. The spatial relationship between a portion of an image and the other images is identified based of the determined spatial arrangement of the images. The method selects a representative image from the plurality of images using, for each image, at least the initial quality value for the image and the accumulated quality value of at least one portion of the image.

22 Claims, 14 Drawing Sheets

(56) References Cited

U.S. PATENT DOCUMENTS

| | | |
|---|---|---|
| 8,224,050 B2 | 7/2012 | Doering et al. |
| 2004/0254477 A1* | 12/2004 | Sekiguchi ................ A61B 3/14 |
| | | 600/476 |
| 2006/0257048 A1 | 11/2006 | Lin |
| 2010/0061601 A1* | 3/2010 | Abramoff .......... G06K 9/00617 |
| | | 382/117 |
| 2011/0267340 A1 | 11/2011 | Kraus et al. |
| 2012/0249956 A1 | 10/2012 | Narasimha-Iyer |
| 2013/0142396 A1* | 6/2013 | Fletcher ................. G06T 7/004 |
| | | 382/106 |

* cited by examiner

OPHTHALMIC REFERENCE IMAGE SELECTION

REFERENCE TO RELATED PATENT APPLICATION(S)

This application claims the benefit under 35 U.S.C. §119 of the filing date of Australian Patent Application No. 2013273657, filed Dec. 18, 2013, hereby incorporated by reference in its entirety as if fully set forth herein.

TECHNICAL FIELD

This invention generally concerns the image stabilization of videos of a retina for image analysis and, in particular, the selection of a single image from a video sequence as a reference image for further alignment and processing.

BACKGROUND

Scanning-laser ophthalmoscopes with adaptive optics (AO/SLO) are medical devices which are becoming increasingly common and increasingly useful for retina imaging. Such devices are able to take microscopic images of a retina with a pixel pitch in the order of microns, and can make the images of individual rods and cones of the eye visible to a doctor.

An image is formed by a device which scans a laser in a raster arrangement over the surface of the retina and senses the amount of light returned. A representative device has a frame rate of around 60 Hz, with a resonant scanner forming scan-lines at a rate of 12 kHz and a pixel clock around 5 MHz, and one representative image size is 400×400 pixels.

By taking a video sequence of images of the retina, instead of still images, the transit of blood cells can be detected, allowing analysis of the velocity of blood flow.

However, AO/SLO can contain substantial image distortion. In a patient who is awake, the eye is in constant motion. One form of this motion is referred to as saccades. Saccades can be extremely fast, causing strong spatial distortions in AO/SLO images. A saccade can cause a rapid translation of the field of view of the retina from image to image, sometimes resulting in shifts between two neighbouring images of more than half the width of the images. When the eye is moving during the raster scanning process, many image distortions are caused, and are analogous to shutter distortion in many modern cameras that use a charge-coupled device (CCD) as an image sensor. Such distortion can cause large changes to the aspect ratio of a single image when motion is in the slow-scan direction of the raster sequence (e.g. between lines), and substantial shearing when motion is in the fast-scan direction of the raster sequence (along a line). If a saccade begins, or ends, or changes direction in the middle of a scan, such distortions may change across the image, or may appear in combination. While it may be possible to analyse the velocity of blood flow with non-aligned images, for many doctors, or for automated software, it is much easier to analyse substantially still images that are well-aligned to a common coordinate system, in order to make a diagnosis.

With many images distorted, it can be difficult to choose a common coordinate system onto which all images should be mapped. One way to achieve such a common coordinate system is to select a relatively undistorted reference image to which all others are mapped. Manual selection of an undistorted reference image can be a tedious and time-consuming process.

When examining methods for selecting a reference image, it is important to distinguish between on-line systems and off-line systems. In an on-line system, images are aligned in real time for immediate display, thus the reference image can only be selected from images that have already occurred, and without knowledge of the position or quality of those images yet to be captured. In an off-line system, where images are processed after all have been collected, the reference image can be selected from all of the gathered images. As more knowledge is available to the selection algorithm, an off-line method can produce a better, albeit less timely, result.

A good reference frame can sometimes be selected by supplementing local quality measures, such as variance and mean intensity, with a mean distance measurement. For example, an on-line system may regard an image as of high quality when the mean distance from that image to recent images is of a smaller value than the mean distance of other images to recent images. However, while the distance between recent images might be small enough, it does not guarantee that a distance between the selected image and other images in a collection of images is acceptable. Furthermore, the mean distance of an image to a collection of images can be problematic in the presence of fast motion such as saccades, where an image falling between widely separated groups of images can have a lower mean distance than an image within one of the groups.

Moreover, while it is theoretically possible for off-line systems to provide a better result in comparison with an on-line approach, to achieve this, the off-line systems might need to exhaustively consider every possible pair of images in the collection, which is not efficient. Therefore, a need exists to provide a system and method for ophthalmic reference image selection in presence of fast motion.

SUMMARY

According to the present disclosure, a representative image is selected on the basis of quality and degree of overlap with other images in a collection of images.

According to one aspect of the present disclosure there is provided a method for selecting a representative image of an eye from a sequence of captured images, the method comprising:

forming at least first and second chains of connected images from the sequence of captured images by associating neighbouring images of the sequence with each other, wherein at least two chains are formed in response to failing to associate at least one pair of neighbouring images, the images in each chain are connected using a relative spatial relationship between the images in the chain;

establishing a spatial relationship between the first and second chains by joining the first and the second chains to form a joined chain, the joining being performed by determining a quality value between a first and a second anchor images, the anchor images being determined using initial quality values for images in the corresponding chain;

determining an accumulated quality value for at least one portion of each image in the joined chain using the initial quality values for images overlapping said portion, wherein an overlapping between a portion of an image and other images being identified based of the established spatial relationship between the chains and the relative spatial relationship between the images in each chain; and selecting a representative image from the joint chain using at least the initial quality value for the image and the determined accumulated quality value for at least one portion of the image.

According to another aspect there is provided a method for selecting a representative image of an eye from a plurality of captured images, the method comprising:

associating neighbouring images from the plurality of images with each other to determine a spatial relationship of the images and an initial quality value for each image;

determining an accumulated quality value for at least one portion of each image using the initial quality values corresponding to those other images of the plurality of images that are spatially related with said portion, the spatial relationship between a portion of an image and the other images being identified based of the determined spatial arrangement of the images; and selecting a representative image from the plurality of images using, for each image, at least the initial quality value for the image and the accumulated quality value of at least one portion of the image.

Generally the selecting is further based on a quality of the images at a position of a portion of an image with the highest determined accumulated quality value across a plurality of portions in the images. More specifically wherein the quality of the image at the position of the portion with the highest determined accumulated quality value is determined based on the initial quality value of said image weighted by relative position of said portion to a centre of said image.

In one implementation the selecting further comprises:

identifying a position of a portion with the highest determined accumulated quality value across the plurality of images;

selecting images spatially associated with the identified position based on the determined spatial relationship of the images; and determining a quality of the selected images at the identified position using the initial quality value of a corresponding image and the identified position relative to a centre of the corresponding image.

Another implementation further comprises:

forming at least two chains of connected images, the connected images being determined using the association of the neighbouring images from the plurality of images with each other, each chain being associated with at least one anchor image;

merging the chains based on at least a quality value between the anchor images of at least two chains; and selecting the representative image from the longest chain of the merged chains of images.

In another implementation, the method further comprises:

forming a quality map by bounding images with the determined spatial relationship;

segmenting the quality map into portions;

determining a quality value of each portion based on the initial quality value of images associated with said portion; and determining a quality of each image in the selected longest chain combining the accumulated quality values of the portions associated with the image.

Preferably, the selecting of the representative image comprises:

determining quality value of a portion of each image using the initial quality values of the images associated with said portion, wherein each initial quality value is weighted by area of overlap between said image and the associated images, the area of overlap being determined based on spatial relationship of the images.

Preferably the quality value is determined for each image of the selected longest chain.

Typically the portion is selected from the group consisting of: a single pixel of the image, a whole image, and an intersection of a plurality of images.

Other aspects are also disclosed.

BRIEF DESCRIPTION OF THE DRAWINGS

At least one embodiment of the invention will now be described with reference to the following drawings, in which.

DETAILED DESCRIPTION INCLUDING BEST MODE

Context

Figure 1:
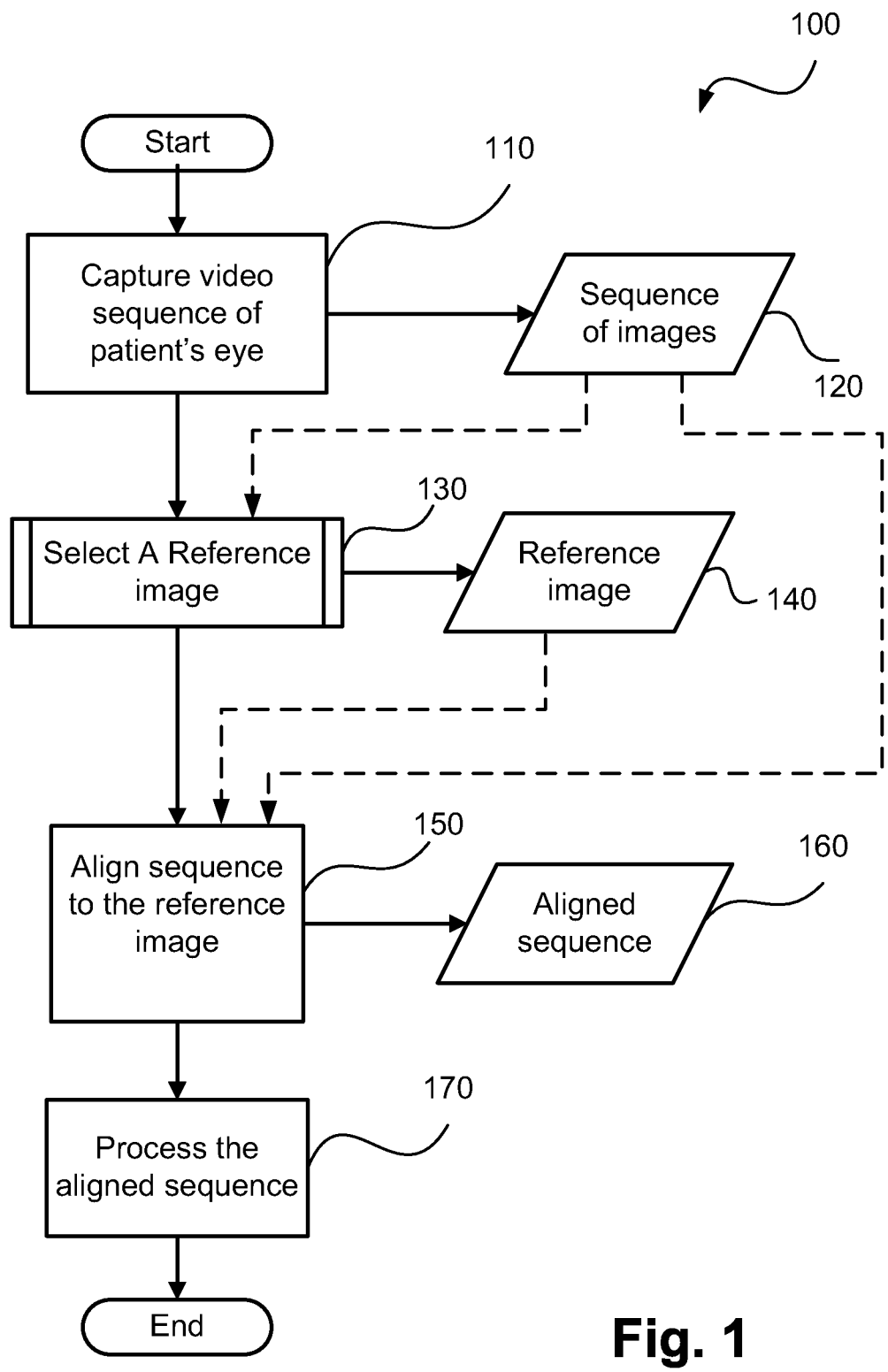
FIG. 1 is a schematic block diagram of an AO/SLO process from acquiring an image sequence from a patient's retina to processing that image sequence for diagnosis.

A process 100 for gathering ophthalmic image sequences for diagnosis is shown in FIG. 1.

In step 110, a patient is seated in front of an AO/SLO device, and requested to look into the device at a fixation point. An attempt is made to capture at least one sequence of images 120, where the images in each sequence are spatially co-located, e.g. the images represent substantially co-located areas of the retina. This can be achieved, for example, by requesting the patient to gaze at a fixation point, or by tracking the retina and reconfiguring the optics to track a single position on the retina. The sequence may be a traditional video sequence captured at traditional frame rates of 25 or 30 frames per second, although other frame rates such as 32 or 64 frames per second may be used. Subject to imaging capability, the sequence may be captured at higher frame rates if desired.

When a sequence of images 120 has been gathered, a reference image 140 is selected at step 130. The reference image 140 is chosen to have high quality and to provide an anchor position to which many other images in the sequence can be aligned.

The reference image 140 should be chosen to have high quality. The assessment of quality of an image is a combination of several characteristics. Firstly, a reference image 140 should have good lighting and contrast characteristics in which the image was gathered through a clear part of the lens of the eye and without occlusion by eyelashes or misplacement by the patient of their pupil. Secondly, a reference image 140 should have low spatial distortion, which is desirable for diagnostic purposes, but also because low distortion is likely to result in higher-quality measurement of spatial distortion against other undistorted images in the image sequence. Thirdly, a reference image 140 should be chosen to be well-positioned spatially within the complete set of images forming the sequence, so that as many images as possible can be aligned to the reference image 140. The metrics related to these characteristics can be referred to as a quality value.

The first two quality characteristics are a local property of the image and can be determined by examination of an image and a few sequentially neighbouring images, for example the two or four immediately adjacent images in the video sequence. The third quality characteristic relates to how an image is placed with respect to a whole set of images from within the sequence, and is typically determined in a number of different ways.

The contrast of an image can be estimated by simple operations such as variance and mean intensity measurements. The spatial distortion of an image can be measured by using one or more two-dimensional correlations, e.g. calculated with a Fast Fourier Transform, to compare a candidate reference image with other images of the sequence. In images which are relatively undistorted and of high quality, the maximum value in the correlation image will be relatively higher. Because it is unlikely that two images would be subject to the same spatial distortion, it is similarly unlikely that two distorted images would result in a large correlation value when a correlation image is calculated.

When the reference image 140 is selected, the reference image 140 is used in step 150 as a spatial reference and aligned through combination with the original sequence 120 to produce an aligned sequence 160, in which aligned images are warped so that common overlapping areas accurately match.

Using this aligned sequence 160, further processing 170 can then occur, such as averaging the aligned images to produce a de-noised image in which photoreceptors can be mapped and counted, or a video sequence in which blood flow can be analysed, or any of many other investigative techniques.

The selection 130 of the reference image 140 is very important to the whole process 100. If the quality of the reference image 140 is low, then the production of the aligned sequence 160 will suffer because the quality of alignment measurement will also suffer. For this reason, it is necessary to use some image quality metric to allow higher quality images to be chosen.

If a particular image contains a substantial spatial distortion, then that image should not be selected as the reference image 140. Spatial distortion adversely affects the alignment measurement, so that if a distorted frame is selected, attempts to align to the reference frame will produce poorer results. Spatial distortion also can have negative effects where an image is used as the basis for subsequent measurement, e.g. of photoreceptor density.

The reference image 140 should also be chosen to have a high degree of overlap, not just with its neighbouring images (images that are close, temporally, in the sequence of the captured images), but with as many high-quality images in the whole sequence as possible. The larger the degree of overlap with other images, then the more images can be included in whatever diagnostic analysis is required and which is typically performed at step 170.

A method for selecting a reference image should take all of these factors into account together in order to produce a good result.

Physical Implementation

Figure 11A:
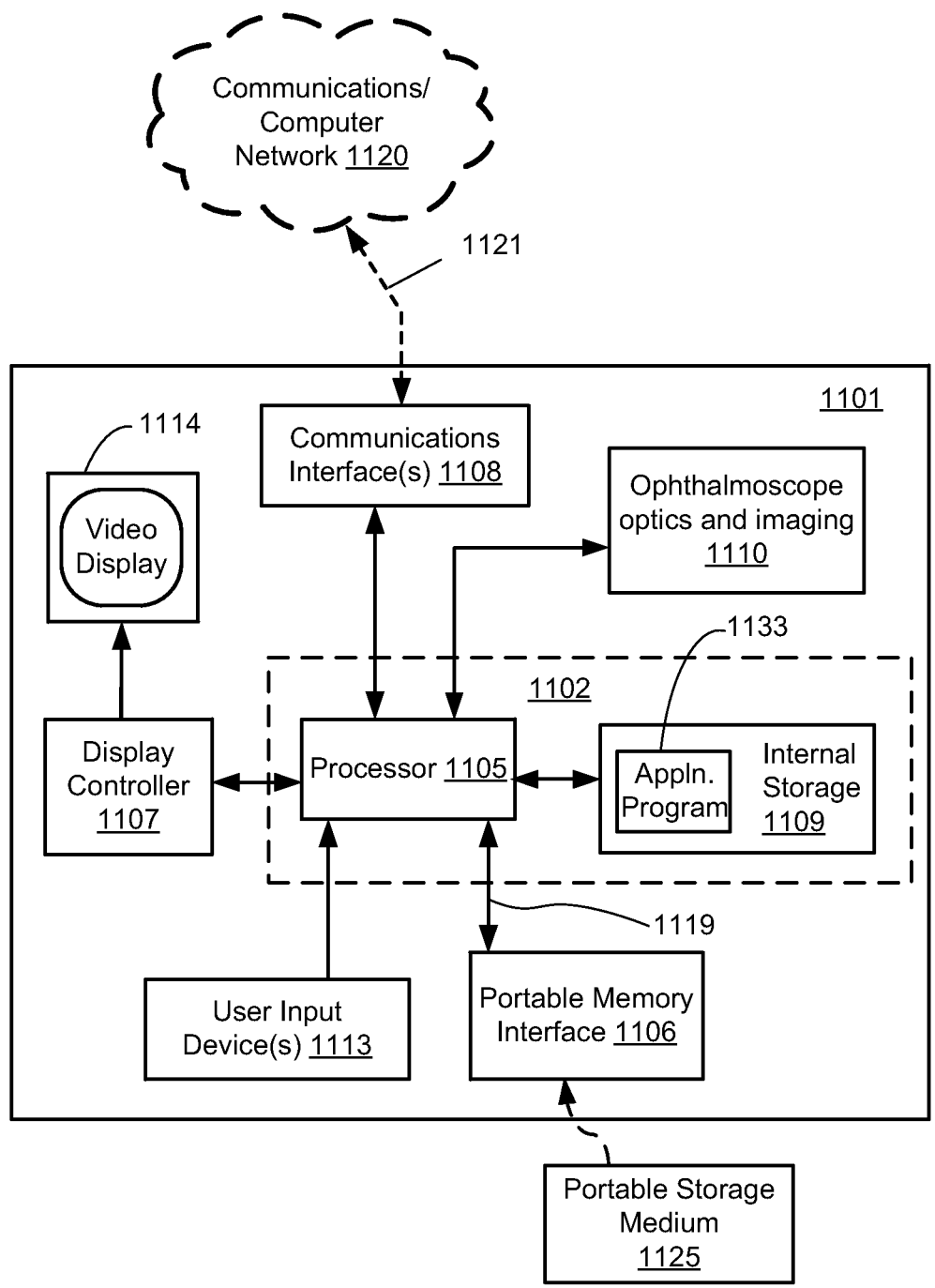
FIGS. 11A and 11B collectively form a schematic block diagram representation of an AO/SLO upon which described arrangements can be practiced.
Figure 11B:
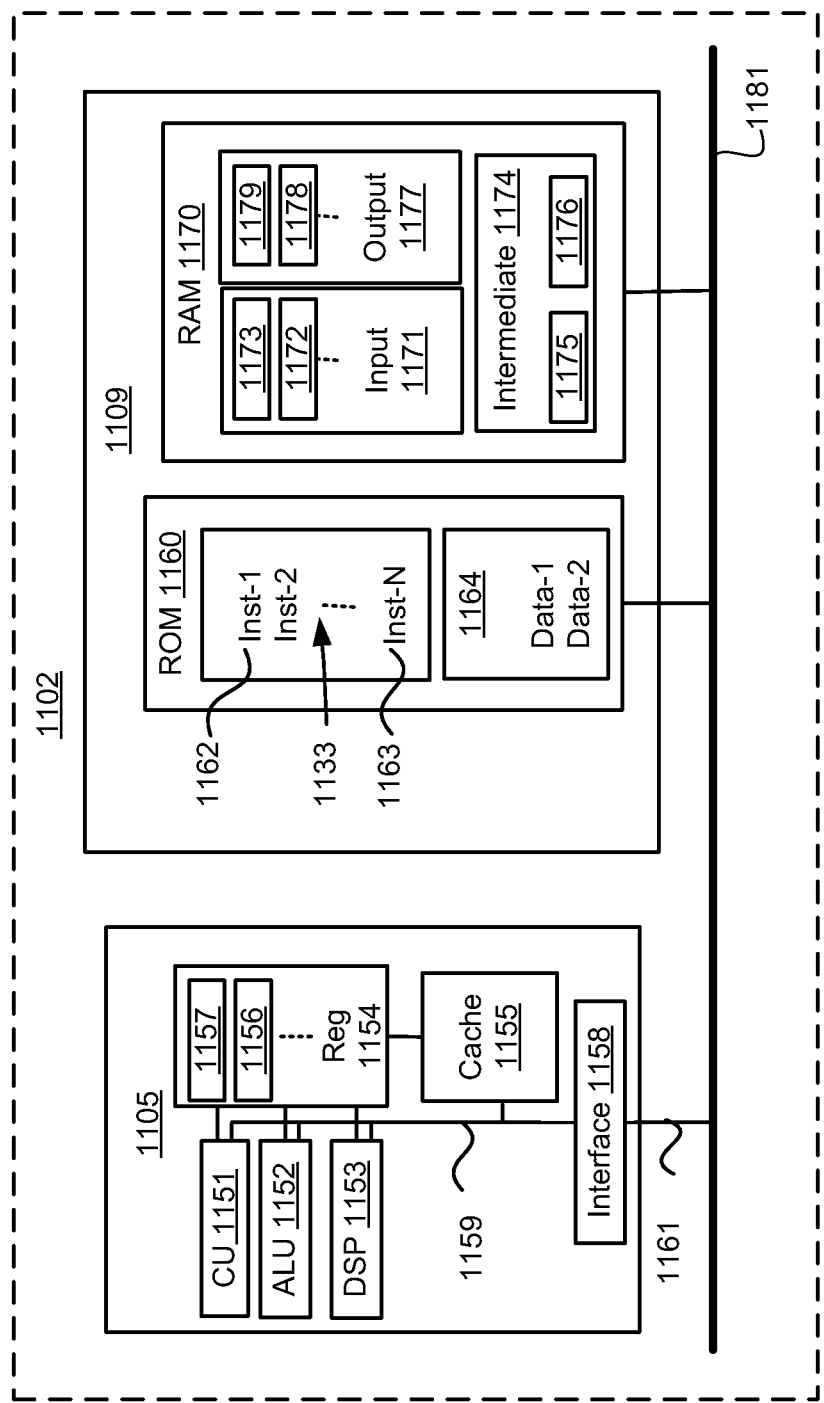

FIGS. 11A and 11B collectively form a schematic block diagram of a scanning laser ophthalmoscope with adaptive optics (AO/SLO) 1101 including embedded components, upon which the representative image selection methods to be described are desirably practiced. Nevertheless, the methods to be described may also be performed on higher-level devices such as desktop computers, server computers, and other such devices with significantly larger processing resources, where for example such devices are simply provided with a video sequence of ophthalmic images.

As seen in FIG. 11A, the AO/SLO 1101 comprises an embedded controller 1102. Accordingly, the AO/SLO 1101 may be referred to as an "embedded device." In the present example, the controller 1102 has a processing unit (or processor) 1105 which is bi-directionally coupled to an internal storage module 1109. The storage module 1109 may be formed from non-volatile semiconductor read only memory (ROM) 1160 and semiconductor random access memory (RAM) 1170, as seen in FIG. 11B. The RAM 1170 may be volatile, non-volatile or a combination of volatile and non-volatile memory.

The AO/SLO 1101 includes a display controller 1107, which is connected to a video display 1114, such as a liquid crystal display (LCD) panel or the like. The display controller 1107 is configured for displaying graphical or bitmap images on the video display 1114 in accordance with instructions received from the embedded controller 1102, to which the display controller 1107 is connected.

The AO/SLO 1101 also includes user input devices 1113 which are typically formed by keys, a keypad or like controls. In some implementations, the user input devices 1113 may include a touch sensitive panel physically associated with the display 1114 to collectively form a touch-screen. Such a touch-screen may thus operate as one form of graphical user interface (GUI) as opposed to a prompt or menu driven GUI typically used with keypad-display combinations. Other forms of user input devices may also be used, such as a microphone (not illustrated) for voice commands or a joystick/thumb wheel (not illustrated) for ease of navigation about menus.

As seen in FIG. 11A, the AO/SLO 1101 also comprises a portable memory interface 1106, which is coupled to the processor 1105 via a connection 1119. The portable memory interface 1106 allows a complementary portable memory device 1125 to be coupled to the AO/SLO 1101 to act as a source or destination of data or to supplement the internal storage module 1109. Examples of such interfaces permit coupling with portable memory devices such as Universal Serial Bus (USB) memory devices, Secure Digital (SD)

cards, Personal Computer Memory Card International Association (PCMIA) cards, optical disks and magnetic disks.

The AO/SLO 1101 also has a communications interface 1108 to permit coupling of the device 1101 to a computer or communications network 1120 via a connection 1121. The connection 1121 may be wired or wireless. For example, the connection 1121 may be radio frequency or optical. An example of a wired connection includes Ethernet. Further, an example of wireless connection includes Bluetooth™ type local interconnection, Wi-Fi (including protocols based on the standards of the IEEE 802.11 family), Infrared Data Association (IrDa) and the like. The network 1120 may form an alternative source of video images for representative image selection.

The embedded controller 1102 is coupled to ophthalmoscope optic and imaging components 1110 to provide for the capture of retinal images preferably as a video sequence. For example, the components 1110 may represent a lens, focus control and imaging sensor of the ophthalmoscope 1101. Where desired, the components 1110 may include a number of image encoders, such as Joint Photographic Experts Group (JPEG) or Moving Picture Experts Group (MPEG). The encoders may be lossy or lossless.

The methods described hereinafter may be implemented using the embedded controller 1102, where the processes of FIGS. 2 to 10 may be implemented as one or more software application programs 1133 executable within the embedded controller 1102. The AO/SLO 1101 of FIG. 11A implements the described methods. In particular, with reference to FIG. 11B, the steps of the described methods are effected by instructions in the software 1133 that are carried out within the controller 1102. The software instructions may be formed as one or more code modules, each for performing one or more particular tasks. The software may also be divided into two separate parts, in which a first part and the corresponding code modules performs the described methods and a second part and the corresponding code modules manage a user interface between the first part and the user.

The software 1133 of the embedded controller 1102 is typically stored in the non-volatile ROM 1160 of the internal storage module 1109. The software 1133 stored in the ROM 1160 can be updated when required from a computer readable medium. The software 1133 can be loaded into and executed by the processor 1105. In some instances, the processor 1105 may execute software instructions that are located in RAM 1170. Software instructions may be loaded into the RAM 1170 by the processor 1105 initiating a copy of one or more code modules from ROM 1160 into RAM 1170. Alternatively, the software instructions of one or more code modules may be pre-installed in a non-volatile region of RAM 1170 by a manufacturer. After one or more code modules have been located in RAM 1170, the processor 1105 may execute software instructions of the one or more code modules.

The application program 1133 is typically pre-installed and stored in the ROM 1160 by a manufacturer, prior to distribution of the AO/SLO 1101. However, in some instances, the application programs 1133 may be supplied to the user encoded on one or more CD-ROM (not shown) and read via the portable memory interface 1106 of FIG. 11A prior to storage in the internal storage module 1109 or in the portable memory 1125. In another alternative, the software application program 1133 may be read by the processor 1105 from the network 1120, or loaded into the controller 1102 or the portable storage medium 1125 from other computer readable media. Computer readable storage media refers to any non-transitory tangible storage medium that participates in providing instructions and/or data to the controller 1102 for execution and/or processing. Examples of such storage media include floppy disks, magnetic tape, CD-ROM, a hard disk drive, a ROM or integrated circuit, USB memory, a magneto-optical disk, flash memory, or a computer readable card such as a PCMCIA card and the like, whether or not such devices are internal or external of the device 1101. Examples of transitory or non-tangible computer readable transmission media that may also participate in the provision of software, application programs, instructions and/or data to the device 1101 include radio or infra-red transmission channels as well as a network connection to another computer or networked device, and the Internet or Intranets including e-mail transmissions and information recorded on Websites and the like. A computer readable medium having such software or computer program recorded on it is a computer program product.

The second part of the application programs 1133 and the corresponding code modules mentioned above may be executed to implement one or more graphical user interfaces (GUIs) to be rendered or otherwise represented upon the display 1114 of FIG. 11A. Through manipulation of the user input device 1113 (e.g., the keypad), a user of the device 1101 and the application programs 1133 may manipulate the interface in a functionally adaptable manner to provide controlling commands and/or input to the applications associated with the GUI(s). Other forms of functionally adaptable user interfaces may also be implemented, such as an audio interface utilizing speech prompts output via loudspeakers (not illustrated) and user voice commands input via the microphone (not illustrated).

FIG. 11B illustrates in detail the embedded controller 1102 having the processor 1105 for executing the application programs 1133 and the internal storage 1109. The internal storage 1109 comprises read only memory (ROM) 1160 and random access memory (RAM) 1170. The processor 1105 is able to execute the application programs 1133 stored in one or both of the connected memories 1160 and 1170. When the AO/SLO 1101 is initially powered up, a system program resident in the ROM 1160 is executed. The application program 1133 permanently stored in the ROM 1160 is sometimes referred to as "firmware". Execution of the firmware by the processor 1105 may fulfil various functions, including processor management, memory management, device management, storage management and user interface.

The processor 1105 typically includes a number of functional modules including a control unit (CU) 1151, an arithmetic logic unit (ALU) 1152 and a local or internal memory comprising a set of registers 1154 which typically contain atomic data elements 1156, 1157, along with internal buffer or cache memory 1155. One or more internal buses 1159 interconnect these functional modules. The processor 1105 typically also has one or more interfaces 1158 for communicating with external devices via system bus 1181, using a connection 1161.

The application program 1133 includes a sequence of instructions 1162 through 1163 that may include conditional branch and loop instructions. The program 1133 may also include data, which is used in execution of the program 1133. This data may be stored as part of the instruction or in a separate location 1164 within the ROM 1160 or RAM 1170.

In general, the processor 1105 is given a set of instructions, which are executed therein. This set of instructions may be organized into blocks, which perform specific tasks or handle specific events that occur in the AO/SLO 1101.

Typically, the application program 1133 waits for events and subsequently executes the block of code associated with that event. Events may be triggered in response to input from a user, via the user input devices 1113 of FIG. 11A, as detected by the processor 1105. Events may also be triggered in response to other sensors and interfaces in the AO/SLO 1101.

The execution of a set of the instructions may require numeric variables to be read and modified. Such numeric variables are stored in the RAM 1170. The disclosed method uses input variables 1171 that are stored in known locations 1172, 1173 in the memory 1170. The input variables 1171 are processed to produce output variables 1177 that are stored in known locations 1178, 1179 in the memory 1170. Intermediate variables 1174 may be stored in additional memory locations in locations 1175, 1176 of the memory 1170. Alternatively, some intermediate variables may only exist in the registers 1154 of the processor 1105.

The execution of a sequence of instructions is achieved in the processor 1105 by repeated application of a fetch-execute cycle. The control unit 1151 of the processor 1105 maintains a register called the program counter, which contains the address in ROM 1160 or RAM 1170 of the next instruction to be executed. At the start of the fetch execute cycle, the contents of the memory address indexed by the program counter is loaded into the control unit 1151. The instruction thus loaded controls the subsequent operation of the processor 1105, causing for example, data to be loaded from ROM memory 1160 into processor registers 1154, the contents of a register to be arithmetically combined with the contents of another register, the contents of a register to be written to the location stored in another register and so on. At the end of the fetch execute cycle the program counter is updated to point to the next instruction in the system program code. Depending on the instruction just executed this may involve incrementing the address contained in the program counter or loading the program counter with a new address in order to achieve a branch operation.

Each step or sub-process in the processes of the methods described below is associated with one or more segments of the application program 1133, and is performed by repeated execution of a fetch-execute cycle in the processor 1105 or similar programmatic operation of other independent processor blocks in the AO/SLO 1101.

Overview

Figure 2:
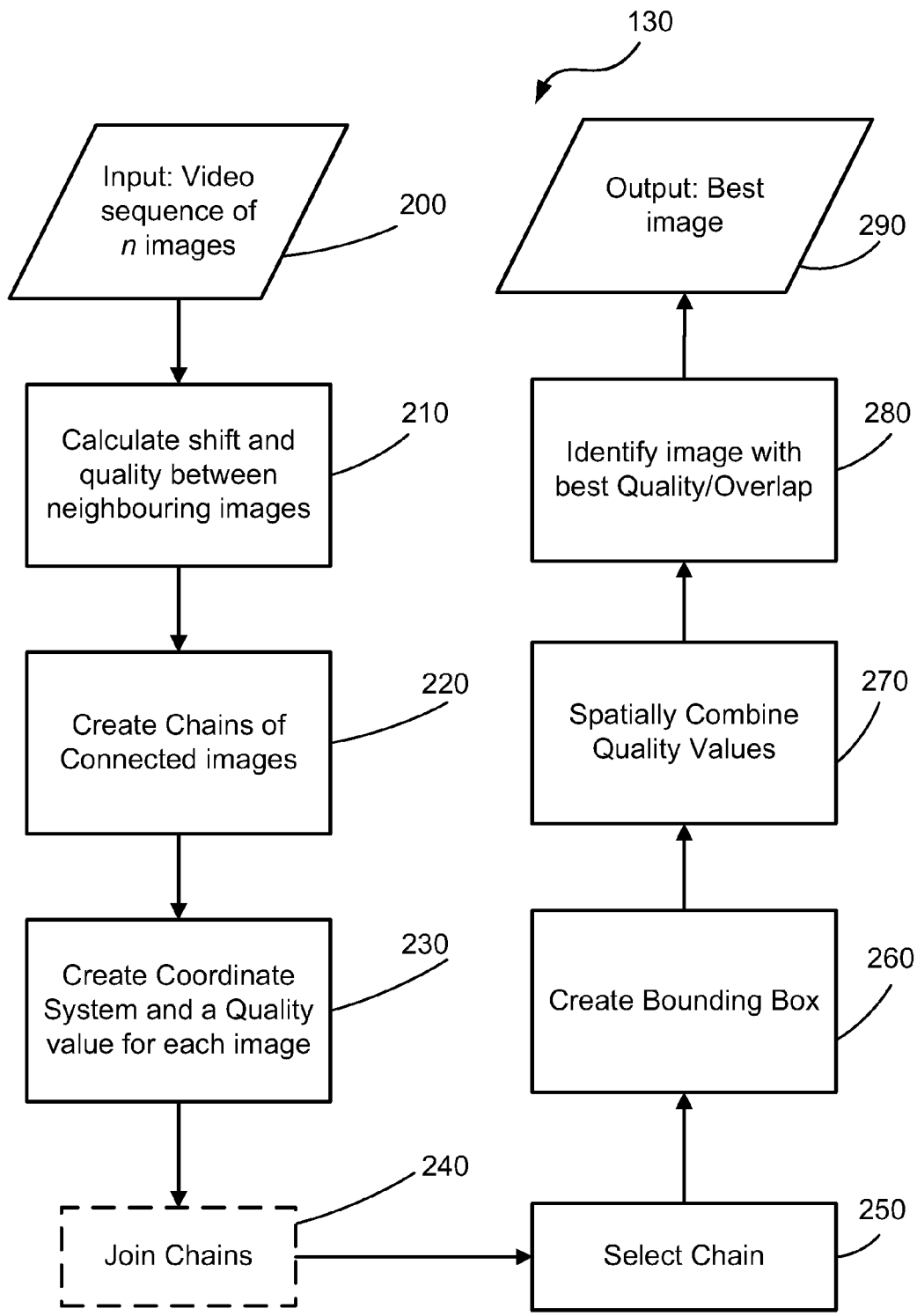
FIG. 2 is a flowchart showing a method for selecting a high-quality reference image from a video sequence of AO/SLO images.

FIG. 2 summarizes a preferred process 130 for the selection of a reference image from a sequence of images, so as to be used for the basis for alignment of images in the sequence. Reference images are selected, where possible, that have a high quality value themselves and also have a large number of high-quality images overlapping them. This allows many high-quality images to be aligned to the reference, and hence aligned to one another. The process 130 is preferably implemented as part of the software application 1133 and executed by the processor 1105.

The input to the process 130 is a sequence of n images 200 captured from the AO/SLO 1101. The images 200 are typically stored upon the internal storage 1109 at the time of capture and may be processed in an off-line fashion by the process 130. Nevertheless, the arrangements disclosed herein are configured for at least some real-time operation through processing images of a sequence whilst such are being captured. A typical sequence 200 may have n=64 to 256 number of images, although the specific number may be chosen to suit the particular application. Alternatively, the images may have been captured remotely and communicated to computer 1101, for example via the networks 1120 or via the recording media 1125, for subsequent processing.

At this point, the images of the retina have no known spatial relationships, other than the likelihood that many of them originate from the same general area, and the likelihood that neighbouring images in the sequence are closer to each other than images in the sequence separated by many other images. A pair of images are neighbours if they are temporally adjacent in the sequence. Except for saccades or deliberate eye movement, the eye tends to only move small distances within a short period of time. When saccades are infrequent, it is reasonable to assume that images that are temporally close are also spatially close.

However, due to saccades, it is possible that two neighbouring images may have no overlapping regions, and it is also possible that there may be multiple regions of the retina represented in the images with no areas of overlap at all, i.e. regions of the retina represented only by a single image.

While it is possible to attempt to directly determine the overlap between every image in a sequence with every other image in the sequence by comparing all possible pairs of images, such an approach is computationally expensive. It is computationally cheaper to build up chains of overlapping neighbouring image frames, as fewer comparisons between images need to be made. If no overlapping is detected, and therefore no connection between images is established, the method 130 may recognize that those neighbouring images belong to different chains and, therefore, will be processed separately. The net effect of this approach is that one sequence of images, obtained from one capture period, may be divided into a number of chains of image frames, being sub-sequences of images that are "connected" in that they at least initially display some amount of overlap between immediately adjacent images in the sub-sequence.

In the first step 210 of the method 130, a relative shift and a quality value estimate are both calculated between each neighbouring pair of images in the sequence(s) in order to assess an association between the neighbouring images. One such quality value is the magnitude of a correlation peak relating the two images. The magnitude of the correlation peak will be attenuated by many effects, and is a reasonable measure of image quality. One effect is poor image quality, such as a dark image from a blink, or partial blink, or a patient moving their head. The magnitude of the peak will be proportional to the overlap area of the two images, and will thus be higher in regions of the sequence where the eye is not moving quickly. The magnitude of the peak will also be attenuated if one or both of the two images contains a strong spatial distortion, such as a shear, a change in aspect ratio, or a rotation.

Another estimate of quality is the ratio between the largest correlation peak value and the second-largest correlation peak value, where the two peaks are distinct. If this ratio is 1.0, then the first peak cannot be said to be any better an estimate of the shift than the first, therefore there is an ambiguity in the shift estimate, and the quality is regarded as low. If this ratio is substantially greater than 1.0, then the correlation peak can be regarded as being well-distinguished from noise, and the peak can be regarded as highly reliable.

By placing thresholds on the peak magnitude and the peak ratio, a lower bound can be placed on the quality of estimates between neighbouring images, with pairs of images with poor-quality estimates (that is, with estimates below the thresholds) being regarded as having failed. Such thresholds can be determined empirically, and can be selected from one of many values depending upon such properties of the image as magnification, scan-rate of the instrument, image size and the features being examined in the eye.

Where a quality estimate is regarded as failed, no spatial information exists between the pair of images involved. This creates a break in a chain of images, possibly terminating one chain, and potentially beginning a new chain.

As well as being used as to produce a quality value, the correlation peak is used to estimate the relative shift between the pair of images. The position of the correlation peak is used to directly determine the shift, with a peak appearing at the origin of the correlation representing no shift between the pair of images, and the displacement of the peak away from the origin directly representing the relative position of the two images. This position can be estimated within a fraction of a pixel by several means already known.

This correlation process is described later with reference to FIG. 7.

Using the calculated shift and quality measures from step 210, step 220 then operates such that pairs of "connected" images are built up into chains, with each image in the chain being connected to the next by an estimate of its relative position, representing an extension of the initial overlap consideration discussed above. Two images are connected in a chain if the threshold test on their quality estimate is regarded as having succeeded, and a chain is broken if the threshold test on quality estimate of two images is regarded as failed. If a later threshold test between another pair of images succeeds, this later pair of images are connected forming a part of another chain. Therefore, a failed threshold test at step 220 can results in at least two chains.

A coordinate system is then created for each chain in step 230, with the top-left corner of the first image in each chain being placed at position (0,0), and each subsequent images placed at an absolute position in this coordinate system based upon the sum of each relative-position estimate leading up to it.

For example, if a chain contains four images, A, B, C, and D, with relative shift estimates for AB=(1.1,2.2), BC=(−0.5,−0.5), CD=(1.5,3.7), then the images can be placed in coordinates relative to A at positions A=(0,0), B=(1.1,2.2), C=(0.6,1.7), and D=(2.1,5.4).

In step 230, a quality value can also be created for each image by combining the quality values previously calculated between each pair of images. For example, the quality value of an image could be the mean value of the successful qualities of the pairs calculated for that image. In this case, a chain containing four images A, B, C, D with quality values for each pair in the chain being AB=10, BC=5, CD=7, the quality value for A is assigned to be 10, B=(10+5)/2=7.5, C=(5+7)/2=6, and D=7. Combining quality values in this way allows one or two quality values related to adjacent pairs of images to be combined within a single image to produce a single quality value for each image in the sequence.

The output from step 230 is a collection of sequences of images, where each image in a sequence is related by a quality value—such a sequence is herein called a "chain". Each image in a chain has a quality value, and a spatial relationship between all images in the same chain is known.

The spatial relationship between images in different chains is, however, not yet known.

Step 240 may be optionally used to attempt to join the disjoint chains into longer chains. At least one image is selected from each chain, for use in joining chains. Typically, a single image, being termed herein an "anchor image", is selected from each chain, by choosing an image with the highest initial quality value in the corresponding chain. However, it is sometimes advantageous to choose more than one image from any one chain, to increase the chance of joining separate chains. In this case, two or more images are chosen from a chain, where the images have high quality values and are not spatially coincident.

The selected anchor images are then paired with selected anchor images from other chains, and a spatial relationship and success status is calculated for each pair. As with the comparisons with neighbours, the spatial relationship and success status can be determined by correlation and examination of the correlation peak in the manner discussed above for step 210 and 220. It is likely that some comparisons will fail, especially if the two images do not overlap in any way.

If a comparison between two images from different chains succeeds, those chains can be linked together. This entails using the shift calculated between the pair of selected images, along with their positions in the coordinate systems of the two unlinked chains. The coordinates in the second chain are offset to align them relative to the coordinates in the first chain. Each joining of two chains will reduce the total number of chains by one.

It is advantageous to link chains together directly after a comparison between two images succeeds. Images can be reselected for the newly linked chain, typically by choosing the single previously-selected image with the highest quality value in the chain. In this way, the number of remaining comparisons between pairs of selected images can be reduced with each joining. It is observed that the joining of chains according to step 240 does not necessarily result in the individual images remaining the order of the original sequence of capture, as in the input sequence 200.

The joining and linking of chains in step 240 might not, and typically would not, result in a single chain being formed. Step 250 selects one chain from the collection of chains produced by step 240. Different criteria can be used to select the chain. One way is to select the longest chain—this is advantageous where it is important to align as many images as possible. Another way is to select a chain with the highest image quality values and a length above some threshold—this is advantageous where aligning a few high quality images is most important. Another way is to select a chain based on the spatial relationship between images in the chain—this is advantageous where it is important to maximize or minimise the estimated area covered by aligned images.

In an application where it is important to register the longest continuous sequence of frames, it can be advantageous to skip step 240. For example, a continuous sequence of registered frames is important for blood flow analysis. Here, step 250 directly selects the longest chain output from step 230.

Step 260 uses the coordinates assigned to each image in the chain selected by step 250 to calculate a bounding box around all images in the chain, including the pixels both in the top left and the bottom right of each image.

Using the bounding box, the coordinate system can be divided into a number of regions. In step 270, quality values associated with the images overlapping each region are combined into a quality measure for that region. This combining may be performed by simple addition.

In step 280, the calculated quality measures are used to select a single image from the longest chain, being that with the best combination of quality and overlap. This is the selected reference or representative image 290 of the input sequence 200, and is the output of the whole process 130.

These steps are now explained in greater detail to allow an effective and efficient implementation. The application of some of these steps to an example sequence of images will also be discussed, with reference to FIGS. 10A to 10C.

First Implementation

This implementation is intended to be operated within the hardware of the AO/SLO device 1101, and will often be performed shortly after the gathering of images from a patient's eyes has completed, so as to provide images to a doctor or analysis program as soon as possible. If the acquisition is of poor quality, or the patient or the device 1101 has not succeeded in creating a view of the desired portion of the retina, then the measurement can be conveniently repeated, or abandoned.

Nevertheless, the method of this implementation may also be performed off-line on historical data, for example sourced from the network 1120, or even on images unrelated to the eye, as this method is as much about selecting high-quality images for later analysis as it is about processing ophthalmic images, where the quality of images can vary markedly during image capture, and where adjacent images are likely to be spatially related yet may be disjoint. In this sense the ophthalmoscope 1101 may be substituted by a general purpose computer.

Figure 3:
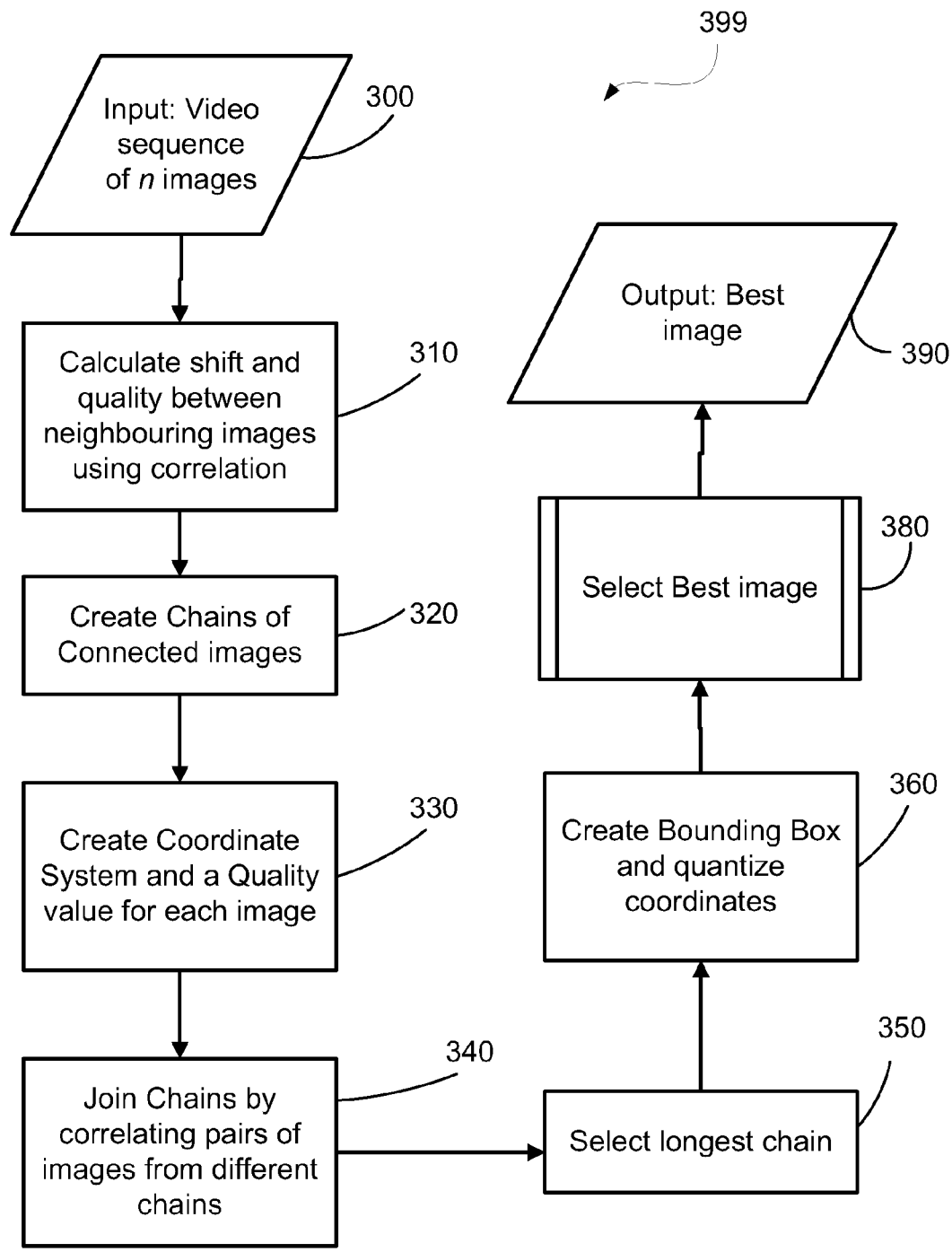
FIG. 3 is a flowchart showing a method for selecting a high-quality reference image from a video sequence of AO/SLO images using a quality map constructed from weighted images.

The description of the method 399 will reference FIG. 3, which is similar to FIG. 2 but with more details concerning this specific implementation.

As input the method takes a sequence of images 300. Images in the sequence are typically captured in the vicinity of the same part of the retina. An image in a sequence of n images may be referred to as $f_i$, where i is a number from 1 to n indicating the order of the image in the sequence. This input 300 can take the form of in-memory images, data files on disk, or images concatenated together into one file.

In step 310, shift and quality are calculated between every pair of adjacent images $f_{i-1}$ and $f_i$. This is performed using a correlation process, as described later in FIG. 9. The output of step 310 includes a success status, either "succeeded" or "failed". If the status is "succeeded", the output also includes a quality value $q_i$ for the match between the pair of images $f_{i-1}$, $f_i$), and a shift vector $S_i=(x_i, y_i)$ representing the displacement between image ($f_{i-1}$, $f_i$).

In step 320, the values of shift and quality are used to assemble the images into chains linked by successful correlations, with each of the images therein having a successful correlation with either a previous or a following image. The first image in each chain is either the first image in the whole sequence, or the first image in a pair in which correlation succeeds after a failure. The last image in each chain is either the second image in a pair in which correlation succeeds immediately before a failure, or the last image in the whole sequence.

There may also be images in which correlation fails with the preceding image and following image. These images are discarded from the image selection process, and are not included in any chain.

In step 330, the quality values and shift values associated with each neighbouring pair of images in a chain is used to calculate a coordinate in a coordinate system for each image, and a quality value for each image.

The quality value for each image in a chain is calculated in two different ways. Where an image has a successful correlation with the previous image and the following image, the quality value $Q_m$ for image $f_m$ is calculated as $$Q_m = \frac{q_m + q_{m+1}}{2}.$$

Where an image has a successful correlation with only one of the previous or following image, the quality value is calculated as either $Q_m=q_m$ or $Q_m=q_{m+1}$. It may be advantageous to increase the quality value for an image which has successful correlations with both the previous and following images by using the definition $$Q_m = \text{weight} \times \frac{q_m + q_{m+1}}{2}$$

or similar, where weight is a factor used to increase the value of the quality value compared to those images that successfully correlate with only one adjacent image. A weight of 1.1 has been found by the inventors to be useful.

The shift values $S_i$ are converted into coordinates $P_i$ by first defining coordinates of the first image in a chain, $f_{first}$, to be $P_{first}=(0,0)$. The coordinates of subsequent images are defined in terms of their predecessor, $P_i=P_{i-1}+S_i$. The x and y coordinates of $P_i$ may be denoted as $P_{ix}$ and $P_{iy}$ respectively.

One preferred quality value desired to be calculated for each image corresponds to the degree of overlap between that image and all other images in the sequence. As there is no information about the spatial relationship between images in different chains, it is advantageous to join separate chains into larger chains. The chain joining step 340 is described later, with reference to FIG. 4.

After the joining process 340 has completed, the longest chain is selected by step 350. This chain will be used to obtain a reference frame.

In step 360, a bounding box is created, within which all the pixels of the images in the longest chain can be placed. The bounding box is calculated using the position and size of all images in the chain, and includes both the minimum and maximum $P_{ix}$ and $P_{iy}$ coordinates.

For reasons of efficiency, all pixel coordinates and image sizes can be divided by some quantization factor and rounded to the nearest integer. All resulting coordinates have the coordinate of the top-left of the bounding box subtracted, to create an origin (0,0) at the top left. A quantization factor of 16, for example, has the effect of reducing the number of pixels to be processed in the method by a factor of 256. These optimizations and simplifications reduce the spatial resolution of the method, but do not appreciably affect the quality of the final result.

Coordinates used in subsequent description are assumed to be in the quantized coordinate space. So if using a quantization factor of 16, for example, images originating from the ophthalmoscope 1101 with size w=200, h=400 will from now on be assumed to be of size w=13, h=25. The size of the bounding box, in quantized coordinate space, is referred to as (W,H).

In step 380, an image is chosen from the chain selected at 350. This image is output as the reference image 390.

Figure 10A:
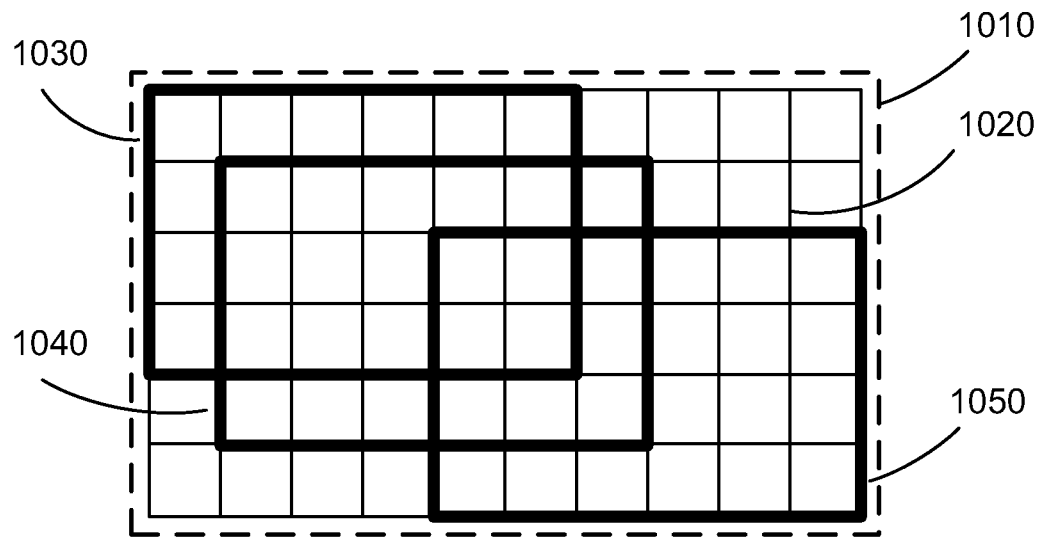
FIGS. 10A to 10C show an example sequence of frames and selection of a frame using a values from a quality map.

FIG. 10A shows an example output of step 360, after steps 300 to 360 are applied to an example sequence of images. In this case, the chain selected at step 350 comprises three spatially associated images, 1030, 1040, and 1050. These images have been spatially positioned and quantized, according to steps 330 to 360. The quantization borders are illustrated by grid 1020. The bounding box 1010 tightly surrounds images 1030 to 1050. The area within bounding box 1010 represents a two-dimensional quality map, described below.

For the present implementation, step 380 will be described as step 380(1) with reference to FIG. 8B. The chain selected at step 350 and bounding box calculated at 360 form an input 850 to the selection process of step 380(1). In a first step 875, a two-dimensional quality map M of size (W, H) is created to spatially combine the quality values from images in the chain selected at step 350. These combined quality values are called quality measures. This quality map is created so as to accumulate by summation the quality values at different positions in the bounding box covered by the images. Regions which are overlapped by many high-quality images will contain a high quality measure, and regions overlapped by only a few low-quality images will contain low quality measures. Regions which are overlapped by other combinations of qualities and quantities will contain quality measures somewhere between these two extremes. The quality map is created of size (W,H), initialized with zero values, and indexed ([0 . . . W−1], [0 . . . H−1]).

The quality value of an image contributes to the quality map where the map and image overlap. It is advantageous, however, for images to contribute a higher quality measure at their centre than at their peripheries. Typically, the quality contribution at the centre of the image is, or is close to, the quality value $Q_i$ of the image. In a later step 885 to identify the best image, a weighting of quality values across an image will favour images centred near a high-quality location over images that are not, all else being equal. A quality value for an image is weighted at different locations within the image using a weighting function. This weighting can be affected by many functions, including those employing a radial distance from the centre of the image. An example weighting function t, suitable for an image of size (w,h), is as follows. For $0 \leq x < w$ and $0 \leq y < h$, $$t(x, y) = \left(1.0 - \frac{|2x - w + 2|}{2w + 1}\right) \times \left(1.0 - \frac{|2y - h + 2|}{2h + 1}\right)$$

For an image $f_i$ of size (w, h) and quality value $Q_i$, a weighted quality-value image $t_i$ can be created which weights the positions in $f_i$ according to quality and how centred they are, $$t_i = Q_i \times t$$

Values from the weighting function t can be pre-calculated in a "template" image of size (w,h), where pixel values in the template image correspond to values in t for each pair (x, y) where $x \in [0, w)$, $y \in [0, h)$.

The quality map is created by summing the weighted quality-value images $t_i$ value into the map image at the determined position of the image in the chain, $$M(x, y) = \sum_{\substack{i: x - P_{ix} \in [0,w), \\ y - P_{iy} \in [0,h)}} t_i(x - P_{ix}, y - P_{iy})$$

A position $B = (B_x, B_y)$ in the quality map M containing the maximum value is identified in step 885 as the position with the maximum quality value.

All of the weighted quality-value images $t_i$ which overlap this position B are examined, and the image with the highest weighted quality measure at this position is selected.

This highest-quality position B can be used to identify an image i that has the highest weighted quality at this position, $$\text{any } i \text{ in} \underset{\substack{i, x, y: B_x - P_{ix} \in [0,w), \\ B_y - P_{iy} \in [0,h)}}{\operatorname{argmax}} (t_i(x - P_{ix}, y - P_{iy}))$$

That is, for each image i overlapping the highest-quality position B, the weighted quality value $Q_i \times t(B_x - P_{ix}, B_y - P_{iy})$ is determined and an image with the highest weighted quality value at position B is selected.

This image $f_i$ is selected to be the selected reference output image 895. For the present implementation, the output image 895 is the output of step 380(1), and the final best image output 390 of the process 399 illustrated in FIG. 3.

Note that it is possible to reorder the order of computation of the intermediate values in this process to improve efficiency, and that it is not necessary for the quality map to be constructed in memory or as a file on disk for the algorithm to operate correctly.

Figure 8A:
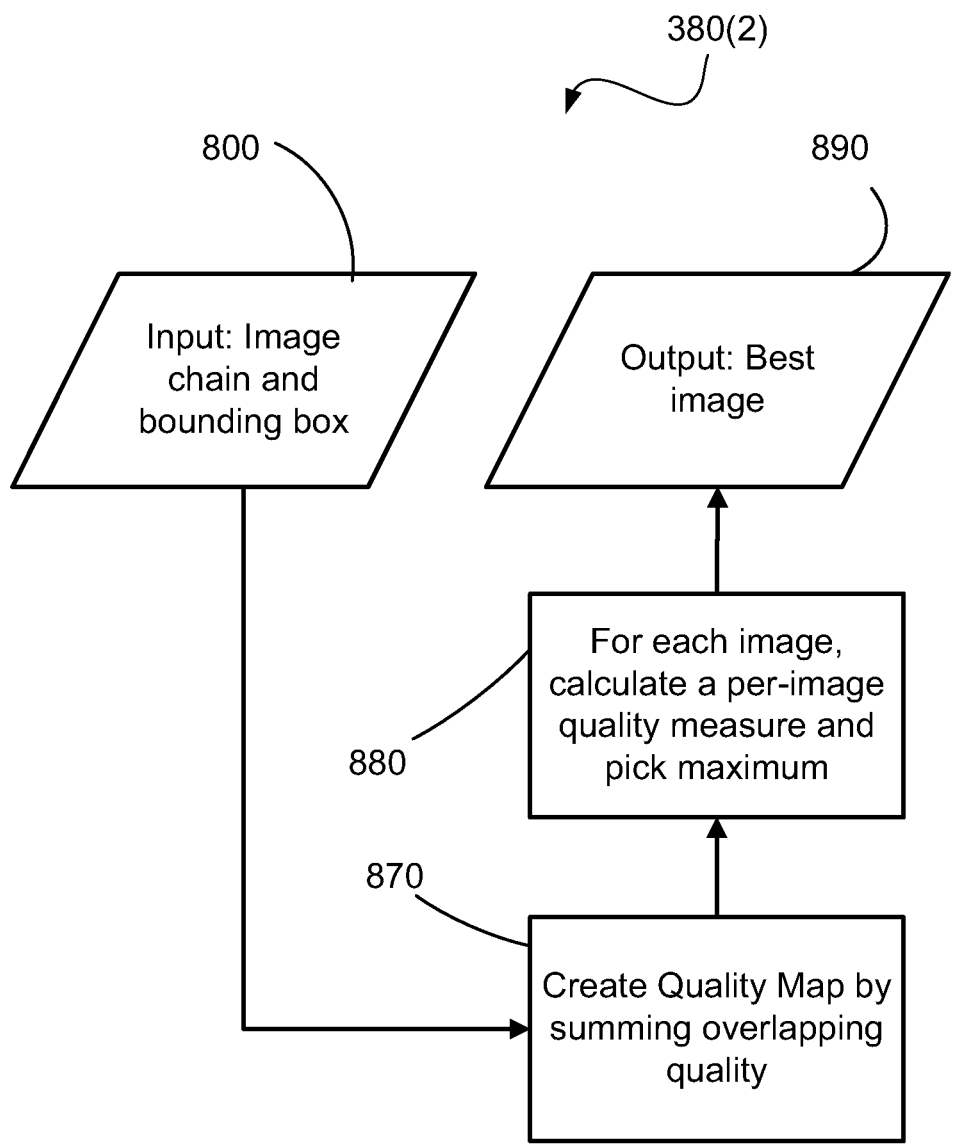
FIG. 8A is a flowchart showing an exemplary method for selecting a high-quality reference image from a chain of images with quality scores.
Figure 8B:
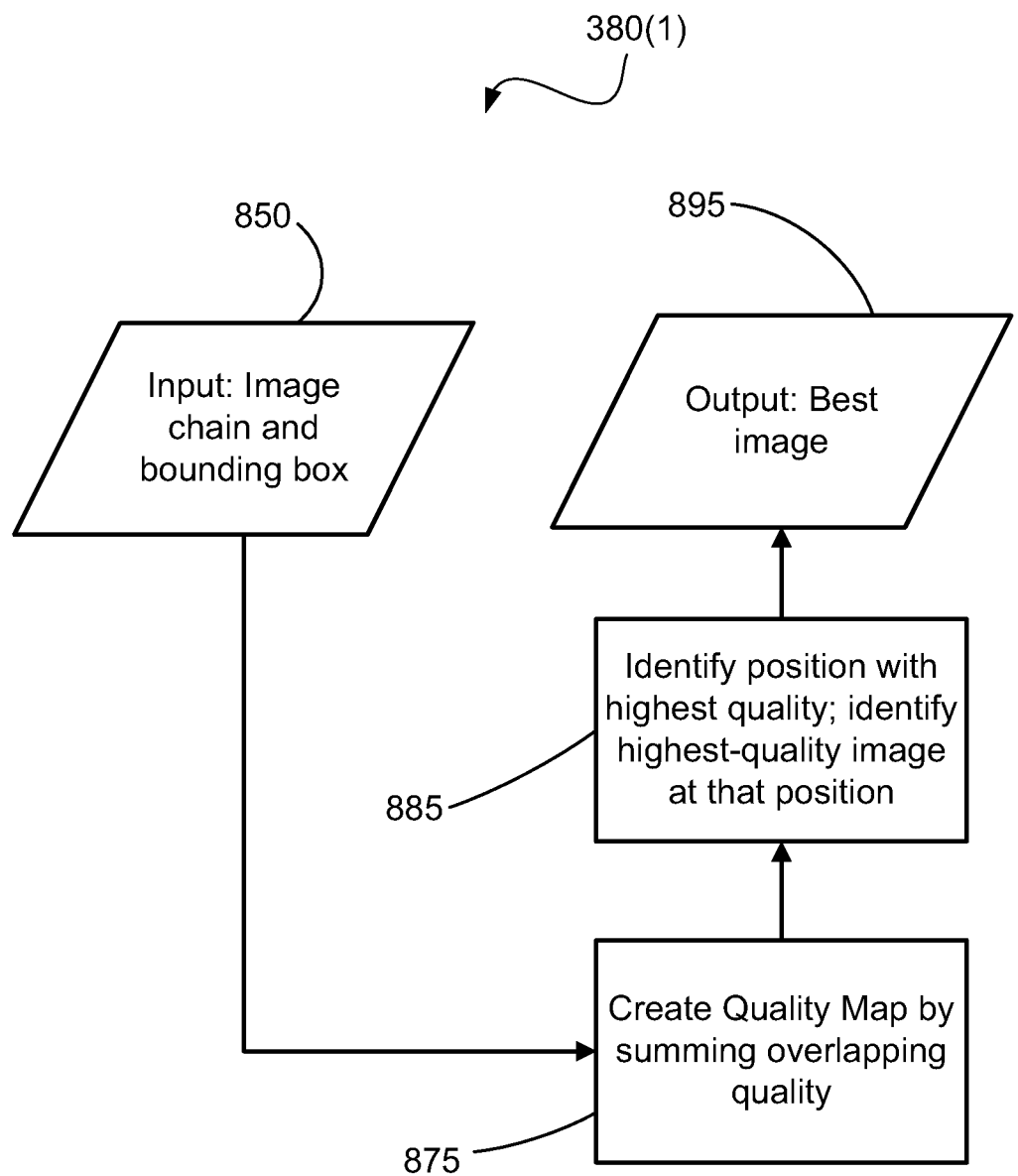
FIG. 8B is a flowchart showing another exemplary method for selecting a high-quality reference image from a chain of images with quality scores.
Figure 10B:
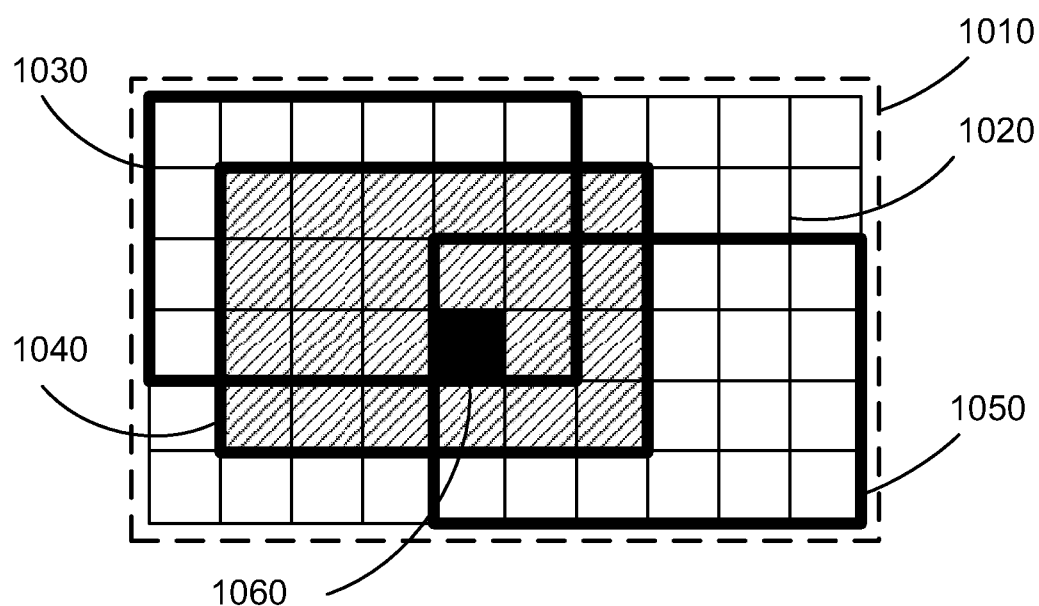

FIG. 10B illustrates the application of steps shown in FIG. 8B to the example chain of images shown in FIG. 10A.

First, the highest-quality position 1060 in the quality map is identified. Next, each image overlapping the highest-quality position 1060 is inspected, and the weighted quality value for each image at position 1060 is determined. An image with the highest weighted quality value at position 1060 is selected. FIG. 10B shows image 1040 as the selected image.

In the example of FIG. 10B, the position 1060 is a single pixel location of the image 1040. The pixel represents a portion of the image 1040, and also of the other images 1030 and 1050. However, the portion of the image considered for the accumulated or weighted quality value need not be a single pixel but can be a group of pixels for which the quality value is, for example, averaged across the group. The portion further need not be regular in shape, such as a rectangular arrangement of pixels, but may for example map an intersection or overlap of the images. The portion in some implementations can be the whole image (i.e. all pixels of the image).

Now some of the sub-procedures in the process of image selection will be described.

Figure 9:
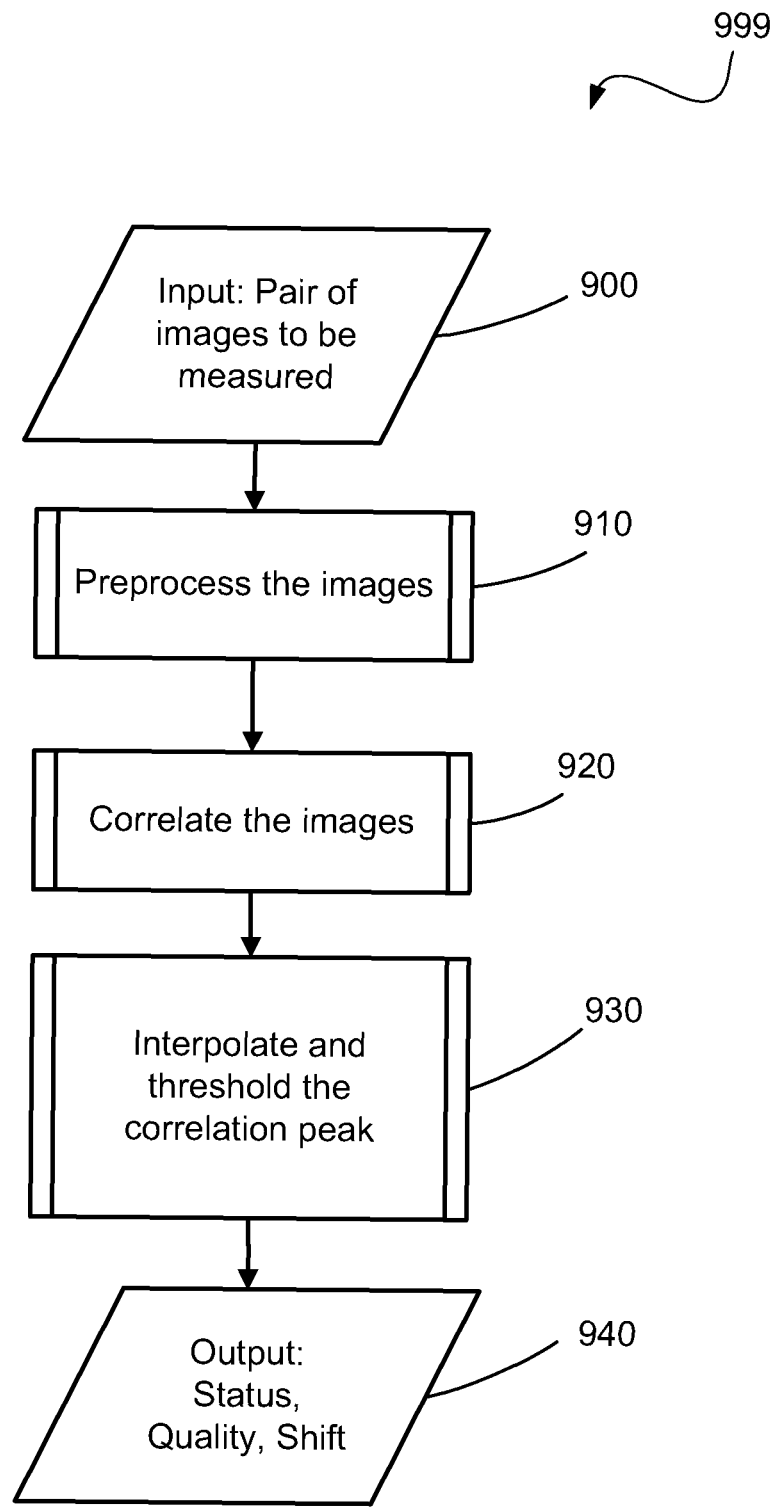
FIG. 9 is a flowchart showing the steps used to match two images using correlation.

FIG. 9 illustrates processes 999 for determining status, shift and quality values from a pair of images performed for example at step 310 and partly performed at step 340.

The input 900 to the process 999 is a pair of images to be compared.

The two images are pre-processed at step 910 before correlation at step 920. The pre-process step 910 is described in more detail in FIG. 5. An image that has been pre-processed at step 910 for a correlation does not need to be pre-processed again for a later correlation. For example, the result of pre-processing an image during execution arising from step 310 can optionally be kept and reused for a later correlation, by skipping step 910 on that image during a later execution arising from either step 310 or step 340.

At step 920, the pre-processed images or input images as the case may be are correlated. The correlation process is described in more detail in FIG. 6.

Any resulting correlation peak is interpolated and compared to a threshold at step 930, and a status, optional shift and quality are returned at step 940. Step 930 is described in more detail in FIG. 7.

Figure 5:
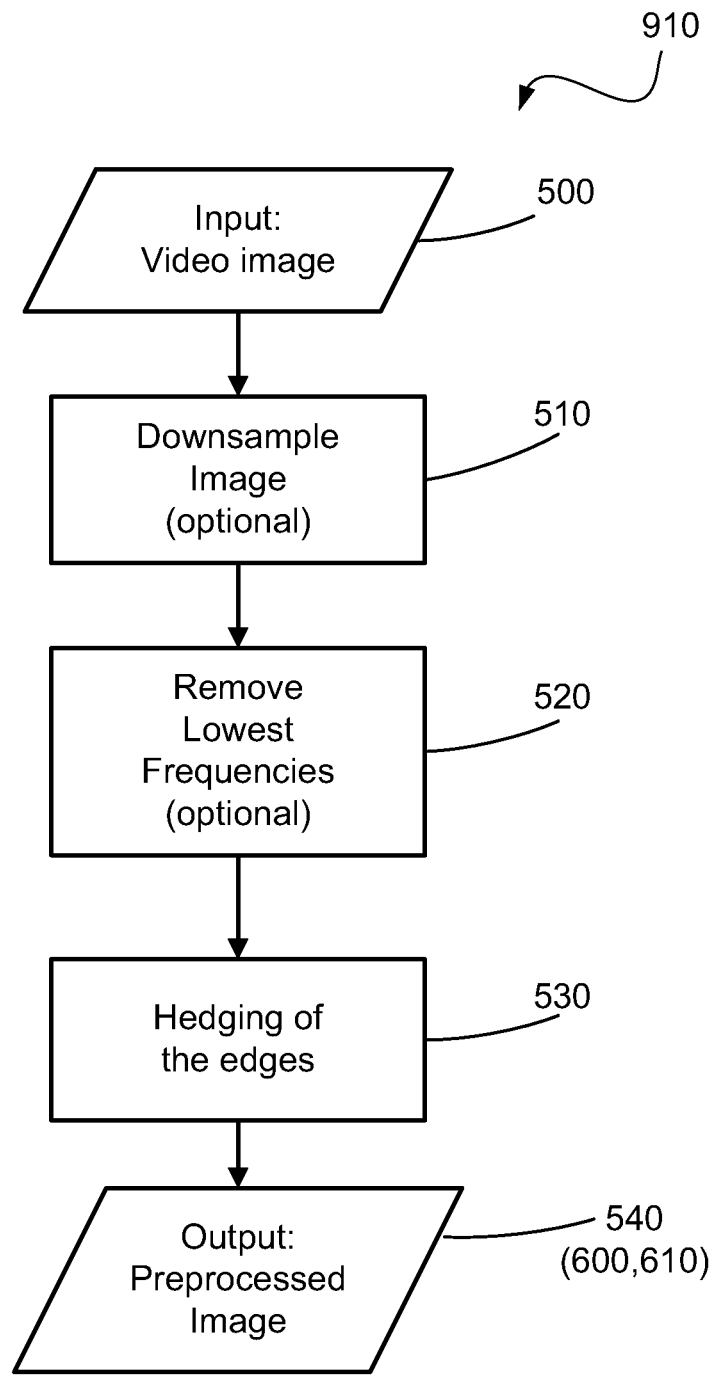
FIG. 5 is a flowchart showing the steps used to pre-process an image in preparation for accurate correlation.

FIG. 5 illustrates a pre-processing process 910 applicable to step 310 in anticipation of correlation. The input to the pre-processor is an image 500. The process 910 is performed, separately and independently, on each image of the pair of images input to the process 310 of FIG. 9. As such, the process 910 lends itself to parallel processing, for example within multiple threads of a multi-processor system implementing the processor 1105.

Where the input images are blurry and/or very noisy, it is usually advantageous, but not essential, to down-sample the image as indicated at step 510 before correlation to remove regions of the Fourier spectrum which contain minimal useful information. A high quality windowed sinc filter can be used for the down-sampling process to ensure that high frequencies are accurately removed, to prevent aliasing, to ensure low frequencies are not attenuated too much, and to ensure that most alignment information is not removed.

To account for possible variations in lighting across each image, it is also advantageous to remove the lowest frequencies from the image, while being careful to treat edges with care, and also make the image zero-mean. This is indicated in the optional step 520 of FIG. 5. Step 520 can be performed using either a high-pass filter, such as one with a spectral response proportional to the distance from the origin, or to subtract a strongly low-passed version of the image, produced either using the mean value of the image, a 2-dimensional polynomial fit with around 5 terms, or a separable convolution by a Gaussian.

The edges of the image are then smoothly reduced in value, a process called hedging, in step 530, to reduce the possibility that the edges of the image will form a strong match in the correlation process. To perform step 530, the m pixels neighbouring the edges of the image can be multiplied by half of a raised-cosine, $$\frac{1-\cos(x*\pi/m)}{2}$$

for x=1, 2, 3 . . . m, representing the distance of each pixel from the edge of the image. A value of m representing 1/16 of the image width produces acceptable results.

The output of this process is a pre-processed image 540.

Given two pre-processed images $g_i$ and $g_{i+1}$, a shift estimation and correlation quality can be calculated by performing a correlation with a spectral weighting to produce a sharp and accurate correlation peak at a position from the origin representing the shift between the two images. An efficient means of computing such a correlation is to use the Fast Fourier Transform, represented by →, and its inverse, represented by ←. The Fourier Transform of the two image tiles $g_i \rightarrow G_i$, and $g_{i+1} \rightarrow G_{i+1}$ is first calculated. The two Fourier transforms are then multiplied together, with the second conjugated, to produce a correlation Fourier transform, $C_i = G_i \times G_{i+1}^*$. To produce a sharp peak, the correlation Fourier transform is optionally multiplied by a spectral weighting equal to the square of the distance of each frequency to the origin, or DC frequency, of the Fourier transform. The inverse Fourier transform of the weighted correlation Fourier transform produces a correlation image, $c_i \leftarrow r^2 \times C_i$, where $r^2$ is the spectral weighting of correlation Fourier transform $C_i$.

Figure 6:
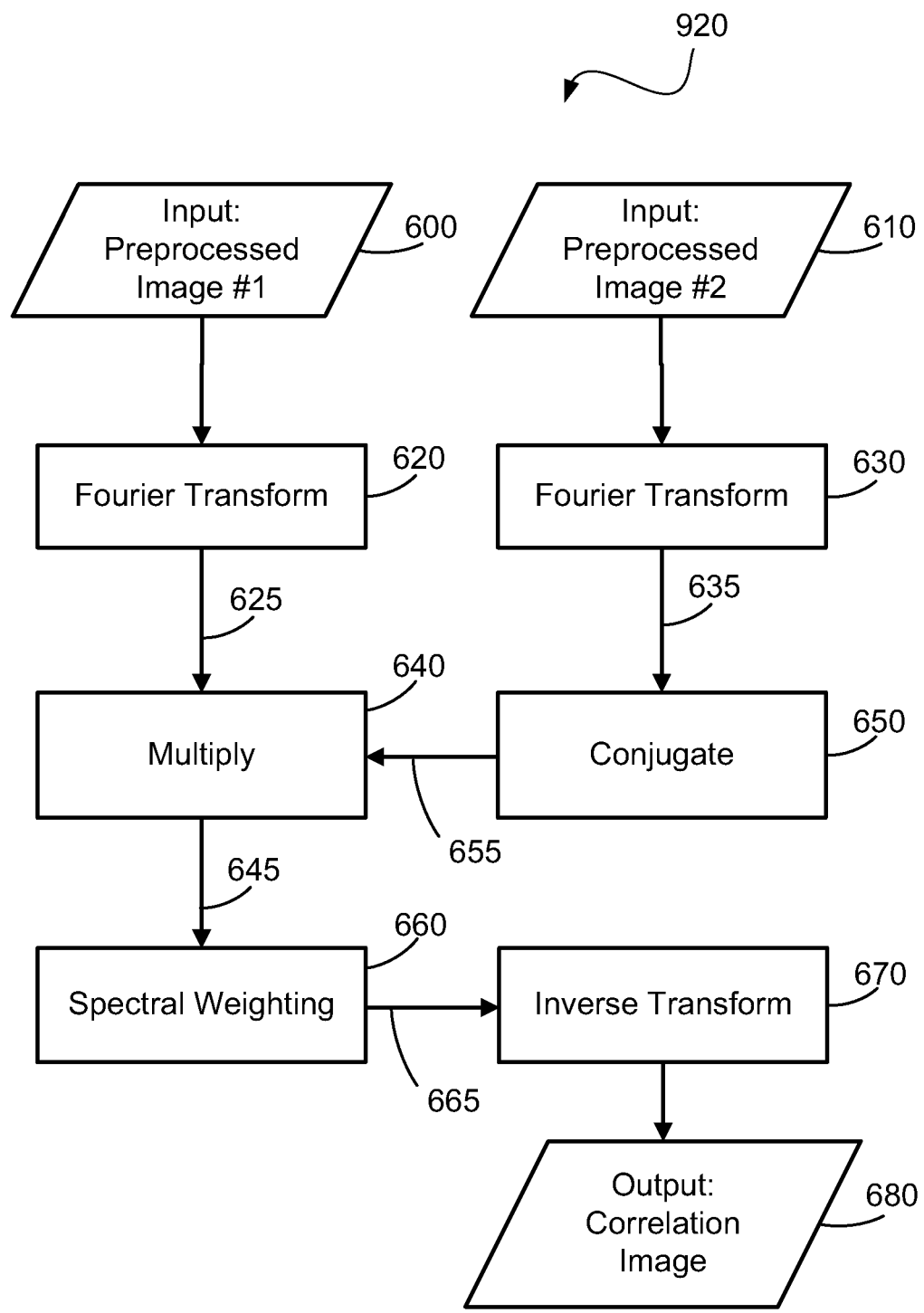
FIG. 6 is a flowchart showing the steps used to correlate two pre-processed images to produce a correlation image.

The process 920 of correlation to produce a correlation image is now described in FIG. 6.

Input to the correlation process is two pre-processed images 600 and 610 produced for respective operation of the process of FIG. 5. A Fourier transform is calculated in steps 620 and 630 for each of the images 600 and 610, producing transformed images 625 and 635. The complex conjugate 655 is calculated at step 650 for the second transformed image 635 and the product of the two images 625 and 655 is calculated at step 640, resulting in a correlation Fourier transform image 645.

Depending upon what pre-processing has been applied to the input images, a spectral weighting 660 can be optionally applied to the correlation Fourier transform image 645 to give a (weighted) transform image 665. An example of a valuable spectral weighting is to multiply the correlation Fourier transform image 645 by a function which is zero at the DC position in the Fourier transform and elsewhere has a value of $r^2$, where r is the distance from the DC position. Another example of a valuable spectral weighting is setting the magnitude of every frequency in the correlation Fourier transform to a constant values, resulting in phase correlation.

An inverse Fourier transform 670 is calculated on the (weighted) correlation Fourier transform image 665, resulting in the output of the process 920, a correlation image 680.

Within a correlation image $c_i$, a correlation peak will usually appear at a distance from the origin corresponding to the displacement between the two correlated images. The position of this peak can be estimated to a fraction of a pixel by up-sampling a region around the peak by a factor of two or four using a high-quality sinc kernel, fitting a parabola to a 3×3 region around the maximum value, and determining an interpolated position for the maximum value by calculating a zero crossing for the derivative of the parabola, which corresponds to its maximum value.

If the pair of input images 600 and 610 match poorly, or not at all, the correlation peak value will be not be appreciably larger than the surrounding values. This can be regarded as a failed match. The reasons for such a failure are many, and may be due to too little signal or too much noise due to blinks or misplacement of the pupil, large spatial distortion in one or both of the images, or because there is little or no overlap of the images. A threshold value can be used to distinguish a match from a non-match. If the correlation peak value is smaller than this threshold value, then the correlation will be regarded as having failed. If the match is regarded as successful, then the correlation peak value can be used directly as a quality value for both images. Because the correlation peak value for a good match depends upon many parameters, such as image size, average pixel value, the amount of image noise, and the amplitude spectrum, this threshold value is best determined by experimentation with real images.

The correlation peak value serves as a good proxy for the quality of the two images involved in the correlation and is used as a quality value for the image pair.

Figure 7:
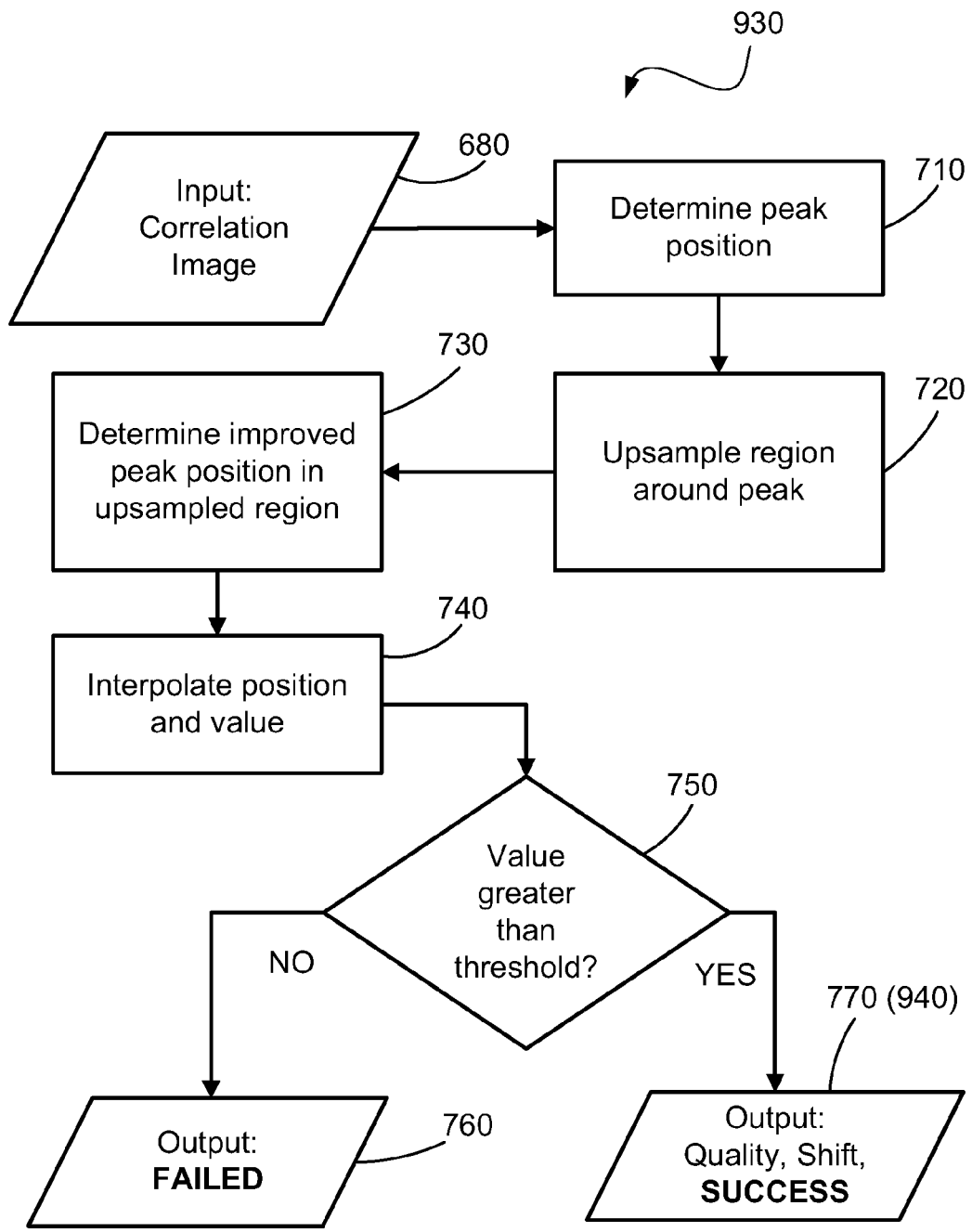
FIG. 7 is a flowchart showing the steps used to measure a correlation image to determine a relative shift between two images, a quality value, and a success/failure status.

FIG. 7 illustrates a process for interpolating the correlation image to determine a status value, and optionally a shift and quality value, as performed at step 930.

Input to the process 930 shown in FIG. 7 is the correlation image 680 produced as described in FIG. 6.

The maximum value in this correlation image 680 is identified, and the position of this maximum value, or correlation peak, is determined, preferably to an accuracy of one pixel at step 710.

A region around this correlation peak is extracted and up-sampled by a factor of either 2 or 4 using a high-quality windowed sinc filter to produce an up-sampled region at step 720. The size of the extracted region should be large enough for accurate interpolation. An extraction region size of 32×32 pixels has been found by the inventors to produce good results.

A new maximum value and position is identified in the up-sampled region at step 730, and this position can be used to resolve the position of the original correlation peak to within 0.5 or 0.25 pixels.

A 3×3 region is then extracted around the new maximum position, and a parabolic fit is used to interpolate an accurate estimate of the position and the value of the peak at step 740. Depending upon the quality and distortion present in the two images, this process can produce an accuracy better than 0.1 pixel.

The interpolated value of the peak is then tested against a threshold value in step 750. If the interpolated value of the peak is smaller than the threshold value, the match is rejected, and the status of "failed" is returned at step 760.

Otherwise, a quality value $q_i$, shift estimate $S_i=(x_i, y_i)$, and a status of "success" is returned at step 770. The quality value $q_i$ is the height of the interpolated peak, and the shift estimation $S_i$ is the position of the interpolated peak.

Figure 4:
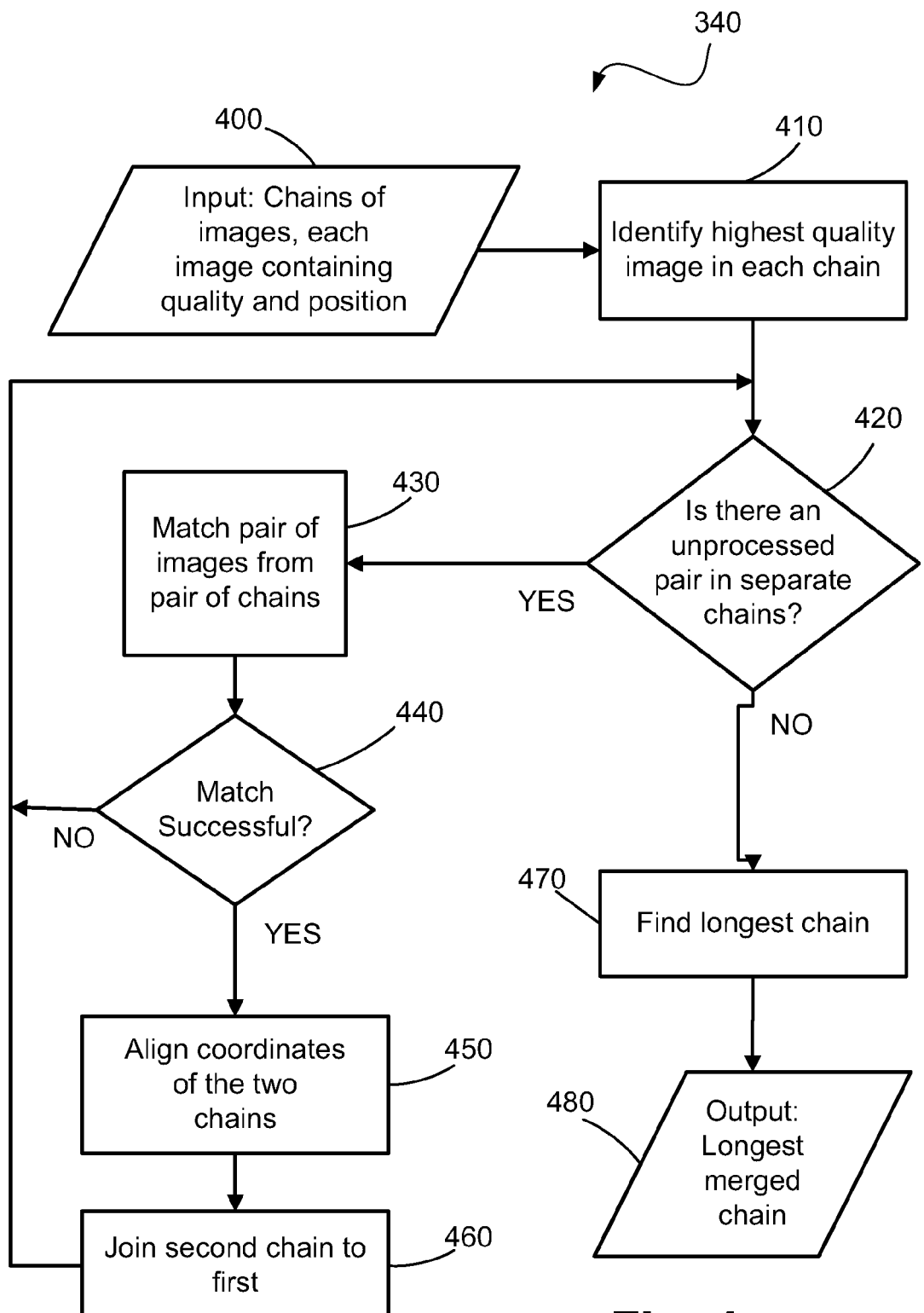
FIG. 4 is a flowchart showing how chains of connected images can be merged together to create longer chains.

The joining process of step 340 used for joining chains together to create longer chains is now described, with reference to FIG. 4.

At the commencement of the joining process 340, as depicted as an input 400, multiple chains exist, with each chain being composed of images, with each image containing a quality value $Q_i$ and a position, relative to the first image in the chain, $P_i$. Because the positions $P_i$ provide only information about relative offsets between the images within a single chain, the positions $P_i$ are not meaningful across the chains, as there is no spatial reference linking the chains together.

Firstly, by using the quality value $Q_i$ already calculated for each image, one image with the largest quality is selected from each chain at step 410. Processing then continues on pairs of images of separate chains.

In step 420, if there is an unprocessed pair m, n of images, where each image is in a separate chain, the pair is matched at step 430 by the procedure 999 described above and for which step 910 can be skipped. The output 940 in this case does not require or determine a "quality", since quality values have already been associated with images during step 330.

If the match at step 430 is unsuccessful, then processing returns to step 420 to process more pairs.

If that match at step 430 is successful, the two chains can be merged into a single chain, as performed in following steps 450 and 460.

In step 450, the coordinates of the two chains are aligned. The coordinates of images in the first chain, containing image m, are left untouched. The coordinates of images in the second chain, containing image n, are offset to align them with the images in the first chain.

Let the image in the first chain have coordinates $P_m$, and the image in the second chain have coordinates $P_n$, and the offset between image m and n be $S_{mn}$. To merge the two chains and have them represented by the same coordinate system, step 460 offsets every image in the second chain by the vector $P_m-P_n+S_{mn}$ to effect the join or merger of the two chains. The previously-selected image with the highest quality of image m and image n remains selected for the newly-merged chain; the other image can be excluded for further testing in step 420.

This joining and merging process can be continued by returning to step 420 until every image pair has been tested, or until every chain has been joined (whichever occurs first).

If more than one chain remains, then the longest chain is selected at step 470, and the other chains discarded.

The output of the chain joining process 340 is the longest chain 480.

Second Implementation

An alternative implementation for choosing a reference image will now be described. This implementation has some different characteristics from that previously described, with reference to FIG. 3. The second implementation has the advantage that a weighting template image is not required, and the quality of positions which overlap an image are calculated differently, and may offer a more efficient implementation.

The two implementations are the same up until the reference frame selection step 380. For this implementation, step 380 will be described with reference to FIG. 8A as step 380(2).

The chain selected at 350 and bounding box calculated at 360 is input 800 to the selection process 380(2).

In step 870, a two-dimensional quality map M of the size of the bounding box (W, H) is created to spatially combine the quality values from the images. This quality map is created so as to accumulate by summation the quality values at different positions in the bounding box covered by the images, resulting in regions which are overlapped by many high-quality images containing a high quality measure, and regions overlapped by few low-quality images containing low quality measure. The quality map is created to be of size (W,H), initialized with zero values, and indexed ([0 . . . W−1], [0 . . . H−1])

No template image is created or used in this process 380(2), contrasting the process 380(1).

For each image in the chain at position $P_i$ with quality value $Q_i$, the quality map is created by summing the quality value of each image into the map image at the determined position of the image in the chain, resulting in a quality measure at each position:

$$M(x, y) = \sum_{\substack{i:\, x-P_{ix}\in[0,w),\\ y-P_{iy}\in[0,h)}} Q_i$$

A per-image quality measure, $V_i$, is then calculated for each image, in step 880.

The per-image quality measure $V_i$ for image $f_i$ is a combination of quality value $Q_i$ and values from the quality map M overlapped by image $f_i$. First, the summation of accumulated quality measures overlapping the image is calculated:

$$O_i = \sum_{\substack{x:\, x-P_{ix}\in[0,w),\\ y:\, y-P_{iy}\in[0,h)}} M(x, y)$$

Since the value at any given position in the quality map M is the summation of quality values from images that overlap that position, the accumulated quality measure for an image is affected by the amount of overlap between that image and other images.

The contribution of image $f_i$ to quality map M is also calculated:

$$N_i = Q_i \times w \times h$$

The per-image quality measure $V_i$ is calculated as the overlapping accumulated quality $O_i$ after removing the image contribution $N_i$, combined with quality value $Q_i$:

$$V_i = Q_i \times (O_i - N_i)$$

The selected image $f_s$ is found by searching for the maximum value, $$s = i, \text{ for which } V_i \text{ is maximized}$$

This image $f_s$ is selected to be the selected reference image output 890. For the present implementation, the output 890 is the output of step 380(2), and the final output 390 of the process illustrated in FIG. 3.

Figure 10C:
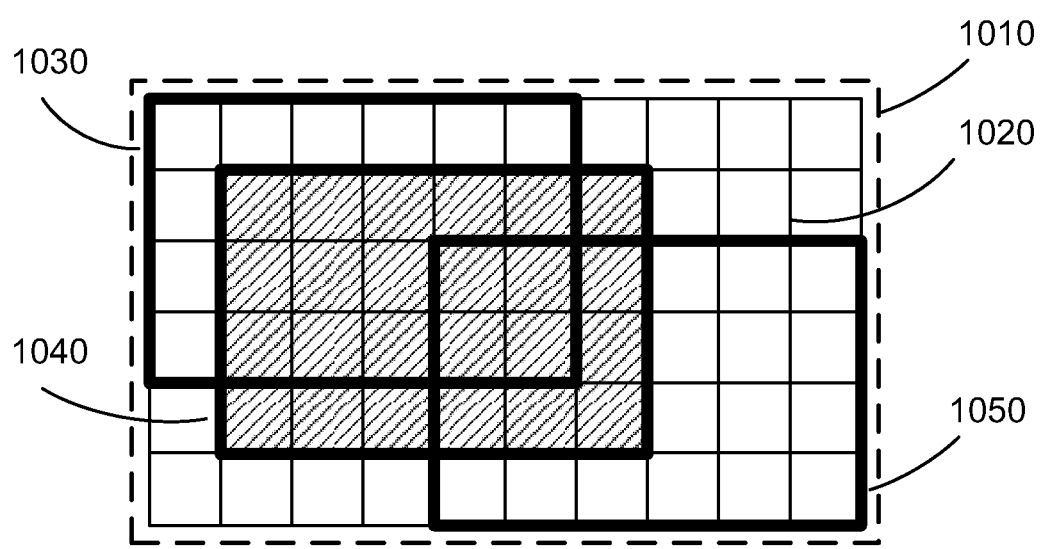

FIG. 10C illustrates the application of steps shown in FIG. 8A to the example chain of images shown in FIG. 10A.

A per-image quality measure is calculated for each of the images 1030 to 1050, as described above. For example, the per-image quality measure for image 1040 is the quality value for image 1040 combined with the sum of quality values contributed to the quality map by images 1030 and 1050 at points in the quality map overlapped by the image 1040. The contribution of images 1030 and 1050 to the quality map overlapped by the image 1040 can be calculated by summing all quality map values overlapped by 1040, then removing the contribution of image 1040. The image with the highest per-image quality measure is selected. FIG. 10C shows image 1040 as the selected image.

In the second implementation described above, $V_i$ is calculated as a quality contribution of other images overlapping $f_i$, weighted by the quality of $f_i$. Other combinations of overlapping area and image quality may be useful for some applications. One example is a linear combination of the quality contribution of image $f_i$ and the quality contribution of other images, $$V_i = \alpha(Q_i \times w \times h) + \beta(O_i - N_i)$$

The quality map M in the above description is used for the efficient mapping of quality values to overlap areas. Another implementation performs substantially the same calculations, without use of the quality map. In this alternative implementation, the quality contribution of an image $f_i$ to the calculation of a per-image quality measure $V_i$ for image $f_i$ is calculated as the quality value $Q_j$ multiplied by the overlapping area between $f_i$ and $f_j$.

INDUSTRIAL APPLICABILITY

The arrangements described are applicable to the computer and data processing industries and particularly for the processing of retinal images, and particularly a sequence of such images.

The foregoing describes only some embodiments of the present invention, and modifications and/or changes can be made thereto without departing from the scope and spirit of the invention, the embodiments being illustrative and not restrictive.

We claim:

1. A method for selecting a representative image of an eye from a sequence of captured images, the method comprising:
    forming at least first and second chains of connected images from the sequence of captured images by associating neighbouring images of the sequence with each other, wherein at least two chains are formed in response to failing to associate at least one pair of neighbouring images, the images in each chain are connected using a relative spatial relationship between the images in the chain;
    establishing a spatial relationship between the first and second chains by joining the first and the second chains to form a joined chain, the joining being performed by determining a quality value between a first and a second anchor images, the anchor images being determined using initial quality values for images in the corresponding chain;
    determining an accumulated quality value for at least one portion of each image in the joined chain using the initial quality values for images overlapping said portion, wherein an overlapping between a portion of an image and other images being identified based of the established spatial relationship between the chains and the relative spatial relationship between the images in each chain; and
    selecting a representative image from the joint chain using at least the initial quality value for the image and the determined accumulated quality value for at least one portion of the image.

2. A method for selecting a representative image of an eye from a plurality of captured images, the method comprising:
    associating neighbouring images from the plurality of images with each other to determine a shift between the images and an initial quality value for each image;
    determining an accumulated quality value for at least one portion of each image using the initial quality values corresponding to those other images of the plurality of images that are spatially related with said portion, the spatial relationship between a portion of an image and the other images being identified based on the shift between the images; and
    selecting a representative image from the plurality of images using, for each image, at least the initial quality value for the image and the accumulated quality value of at least one portion of the image.

3. A method according to claim 2, wherein the selecting is further based on a quality of the images at a position of a portion of an image with the highest determined accumulated quality value across a plurality of portions in the images.

4. A method according to claim 3, wherein the quality of the image at the position of the portion with the highest determined accumulated quality value is determined based on the initial quality value of said image weighted by relative position of said portion to a centre of said image.

5. A method according to claim 2, wherein the selecting further comprises:
    identifying a position of a portion with the highest determined accumulated quality value across the plurality of images;
    selecting images spatially associated with the identified position based on the determined spatial relationship of the images; and
    determining a quality of the selected images at the identified position using the initial quality value of a corresponding image and the identified position relative to a centre of the corresponding image.

6. A method according to claim 2, further comprising:
    forming at least two chains of connected images, the connected images being determined using the association of the neighbouring images from the plurality of images with each other, each chain being associated with at least one anchor image;
    merging the chains based on at least a quality value between the anchor images of at least two chains; and
    selecting the representative image from the longest chain of the merged chains of images.

7. A method according to claim 2, further comprising:
    forming a quality map by bounding images with the determined spatial relationship;

segmenting the quality map into portions;
determining a quality value of each portion based on the initial quality value of images associated with said portion; and
determining a quality of each image in the selected longest chain combining the accumulated quality values of the portions associated with the image.

8. A method according to claim 2, wherein the selecting of the representative image comprises:
determining quality value of a portion of each image using the initial quality values of the images associated with said portion, wherein each initial quality value is weighted by area of overlap between said image and the associated images, the area of overlap being determined based on the determined shift between the images.

9. A method according to claim 8, wherein the quality value is determined for each image of the selected longest chain.

10. A method according to claim 2 wherein the portion is selected from the group consisting of: a single pixel of the image, a whole image, and an intersection of a plurality of images.

11. A method according to claim 2, wherein the initial quality is determined based on a magnitude of a correlation peak associated with the determined shift.

12. A method according to claim 2, wherein the accumulated quality value for a portion of an image is determined using the initial quality values of images overlapping said portion, wherein each initial quality value is weighted by an area of overlap between said portion and a respective image overlapping said portion.

13. A method according to claim 2, wherein the plurality of images in each sequence are spatially co-located.

14. A non-transitory computer readable storage medium having a program recorded thereon, the program being executable by a processor to select a representative image of an eye from a plurality of captured images, the program comprising:
code for associating neighbouring images from the plurality of images with each other to determine a shift between the images and an initial quality value for each image;
code for determining an accumulated quality value for at least one portion of each image using the initial quality values corresponding to those other images of the plurality of images that are spatially related with said portion, the spatial relationship between a portion of an image and the other images being identified based on the shift between the images; and
code for selecting a representative image from the plurality of images using, for each image, at least the initial quality value for the image and the accumulated quality value of at least one portion of the image.

15. A non-transitory computer readable storage medium according to claim 14, wherein the selecting is further based on a quality of the images at a position of a portion of an image with the highest determined accumulated quality value across a plurality of portions in the images and the quality of the image at the position of the portion with the highest determined accumulated quality value is determined based on the initial quality value of said image weighted by relative position of said portion to a centre of said image.

16. A non-transitory computer readable storage medium according to claim 14, wherein the code for selecting further comprises:
code for identifying a position of a portion with the highest determined accumulated quality value across the plurality of images;
code for selecting images spatially associated with the identified position based on the determined spatial relationship of the images; and
code for determining a quality of the selected images at the identified position using the initial quality value of a corresponding image and the identified position relative to a centre of the corresponding image.

17. A non-transitory computer readable storage medium according to claim 14, further comprising:
code for forming at least two chains of connected images, the connected images being determined using the association of the neighbouring images from the plurality of images with each other, each chain being associated with at least one anchor image;
code for merging the chains based on at least a quality value between the anchor images of at least two chains; and
code for selecting the representative image from the longest chain of the merged chains of images.

18. A non-transitory computer readable storage medium according to claim 14, further comprising:
code for forming a quality map by bounding images with the determined spatial relationship;
code for segmenting the quality map into portions;
code for determining a quality value of each portion based on the initial quality value of images associated with said portion; and
code for determining a quality of each image in the selected longest chain combining the accumulated quality values of the portions associated with the image.

19. A non-transitory computer readable storage medium according to claim 14, wherein the code for selecting of the representative image comprises:
code for determining quality value of a portion of each image using the initial quality values of the images associated with said portion, wherein each initial quality value is weighted by area of overlap between said image and the associated images, the area of overlap being determined based on the determined shift between the images, wherein the quality value is determined for each image of the selected longest chain.

20. A non-transitory computer readable storage medium according to claim 14 wherein the portion is selected from the group consisting of: a single pixel of the image, a whole image, and an intersection of a plurality of images.

21. Ophthalmic imaging apparatus comprising imaging components configured to capture a sequence of images of an eye, a processor, a memory coupled to the processor for storing the sequence of images and a program, the program being executable by the processor for selecting a representative image of the eye from the sequence of captured images, the program comprising:
code for forming at least first and second chains of connected images from the sequence of captured images by associating neighbouring images of the sequence with each other, wherein at least two chains are formed in response to failing to associate at least one pair of neighbouring images, the images in each chain are connected using a relative spatial relationship between the images in the chain;
code for establishing a spatial relationship between the first and second chains by joining the first and the second chains to form a joined chain, the joining being performed by determining a quality value between a first and a second anchor images, the anchor images being determined using initial quality values for images in the corresponding chain;

code for determining an accumulated quality value for at least one portion of each image in the joined chain using the initial quality values for images overlapping said portion, wherein an overlapping between a portion of an image and other images being identified based of the established spatial relationship between the chains and the relative spatial relationship between the images in each chain; and code for selecting a representative image from the joint chain using at least the initial quality value for the image and the determined accumulated quality value for at least one portion of the image.

22. Ophthalmic imaging apparatus comprising imaging components configured to capture a sequence of images of an eye, a processor, a memory coupled to the processor for storing the sequence of images and a program, the program being executable by the processor for selecting a representative image of an eye from a plurality of captured images, the program comprising:

code for associating neighbouring images from the plurality of images with each other to determine a shift between the images and an initial quality value for each image;

code for determining an accumulated quality value for at least one portion of each image using the initial quality values corresponding to those other images of the plurality of images that are spatially related with said portion, the spatial relationship between a portion of an image and the other images being identified based on the determined shift between the images; and code for selecting a representative image from the plurality of images using, for each image, at least the initial quality value for the image and the accumulated quality value of at least one portion of the image.

* * * * *